US011786565B2

(12) United States Patent
Hu et al.

(10) Patent No.: US 11,786,565 B2
(45) Date of Patent: Oct. 17, 2023

(54) **STRAINS OF *LACTOBACILLUS DELBRUECKII* WHICH INHIBIT *PORPHYROMONAS GINGIVALIS***

(71) Applicant: Trustees of Tufts College, Boston, MA (US)

(72) Inventors: Linden Hu, Sharon, MA (US); Louis Cornacchione, Cambridge, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 17/440,747

(22) PCT Filed: Mar. 18, 2020

(86) PCT No.: PCT/US2020/023454
§ 371 (c)(1),
(2) Date: Sep. 17, 2021

(87) PCT Pub. No.: WO2020/191111
PCT Pub. Date: Sep. 24, 2020

(65) Prior Publication Data
US 2022/0193153 A1 Jun. 23, 2022

Related U.S. Application Data

(60) Provisional application No. 62/837,690, filed on Apr. 23, 2019, provisional application No. 62/820,210, filed on Mar. 18, 2019.

(51) Int. Cl.
| | |
|---|---|
| *A61K 35/744* | (2015.01) |
| *A61P 1/02* | (2006.01) |
| *C12N 1/20* | (2006.01) |
| *A61K 35/74* | (2015.01) |
| *A61K 35/00* | (2006.01) |

(52) U.S. Cl.
CPC ............ *A61K 35/744* (2013.01); *A61K 35/74* (2013.01); *A61P 1/02* (2018.01); *C12N 1/205* (2021.05); *A61K 2035/115* (2013.01)

(58) Field of Classification Search
None
See application file for complete search history.

(56) References Cited

U.S. PATENT DOCUMENTS

| | | | | |
|---|---|---|---|---|
| 4,965,194 A | * | 10/1990 | Yamamoto | ........... C12N 9/0008 435/189 |
| 9,676,641 B2 | | 6/2017 | Parsley et al. | |
| 9,730,883 B2 | * | 8/2017 | Okumura | ............... A61Q 11/00 |

FOREIGN PATENT DOCUMENTS

JP 5544234 * 7/2014

OTHER PUBLICATIONS

Leke et al. "Effects of hydrogen peroxide in growth and selected properties of Porphyromonas gingivalis". FEMS Microbiology Letters, 199, 174, pp. 347-353.*
Cunningham et al. Journal of Biological Chemistry, 1971, 246 (6), pp. 1575-1582; STN CAPLUS abstract, one page.*
Kobayashi, R., et al. "Oral administration of Lactobacillus gasseri SBT2055 is effective in preventing Porphyromonas gingivalis-accelerated periodontal disease." *Scientific reports* 7.1 (2017): 1-10.
Bermúdez-Humarán, Luis G., et al. "Lactococci and lactobacilli as mucosal delivery vectors for therapeutic proteins and DNA vaccines." Microbial cell factories 10.1 (2011): 1-10.
Wells, Jerry M., and Annick Mercenier. "Mucosal delivery of therapeutic and prophylactic molecules using lactic acid bacteria." Nature Reviews Microbiology 6.5 (2008): 349-362.
Grangette, Corinne, et al. "Enhanced mucosal delivery of antigen with cell wall mutants of lactic acid bacteria." Infection and immunity 72.5 (2004): 2731-2737.
Cornacchione, Louis P., et al. "Interspecies Inhibition of Porphyromonas gingivalis by yogurt-derived Lactobacillus delbrueckii requires active pyruvate oxidase." Applied and environmental microbiology 85.18 (2019): e01271-19.
Duncan, Margaret, NIH Abstract for Grant No. DE024308, funded on Mar. 25, 2014.
Cornacchione, Louis, NIH Abstract for Grant No. DE025523 funded on Mar. 4, 2016.
International Search Report issued in International Application No. PCT/US2020/023454, dated Jun. 17, 2020.
Hillman, et al., "Interaction between wild-type, mutant and revertant forms of the bacterium *Streptococcus sanguis* and the bacterium *Actinobacillus actinomycetemcomitans* in vitro and in the gnotobiotic rat," *Archives of Oral Biology* 1988;33(6):395-401.
Liu, et al., "Function of the pyruvate oxidase-lactate oxidase cascade in interspecies competition between *Streptococcus oligofermentans* and *Streptococcus mutans,*" *Applied and environmental microbiology* Apr. 2012;78(7):2120-7.
Sedewitz, et al., "Purification and biochemical characterization of pyruvate oxidase from Lactobacillus plantarum," *Journal of Bacteriology*, Oct. 1984; 160(1): 273-278.
Zheng, et al., "Oxygen dependent pyruvate oxidase expression and production in *Streptococcus sanguinis,*" *International Journal of Oral Science*, (2011) retrieved online: URL: https://www.sigmaaldrich.eom/US/en/tech-docs/paper/183148.

* cited by examiner

*Primary Examiner* — Vera Afremova
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are compositions and methods for treating periodontal disease.

12 Claims, 27 Drawing Sheets
Specification includes a Sequence Listing.

| STYM1 Lysate | +Pyruvate, PO₄ | +Pyruvate, PO₄, FAD, TPP, Mn⁺² | +Lactate, TPP, FAD |
|---|---|---|---|
| 7.33mm ± 0.1667 | 9.167mm ± 0.1667 | 10.33mm ± 0.3333 | 8.833mm ± 0.3333 |

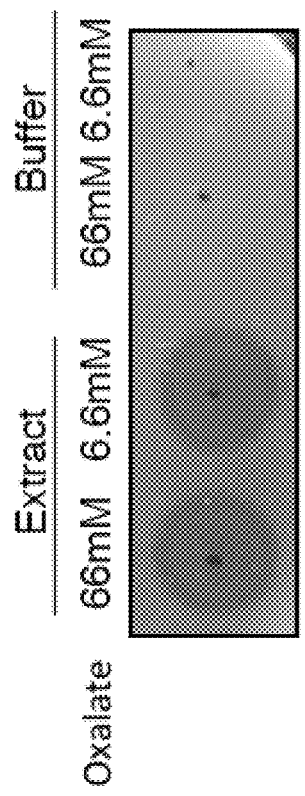
FIG. 6B
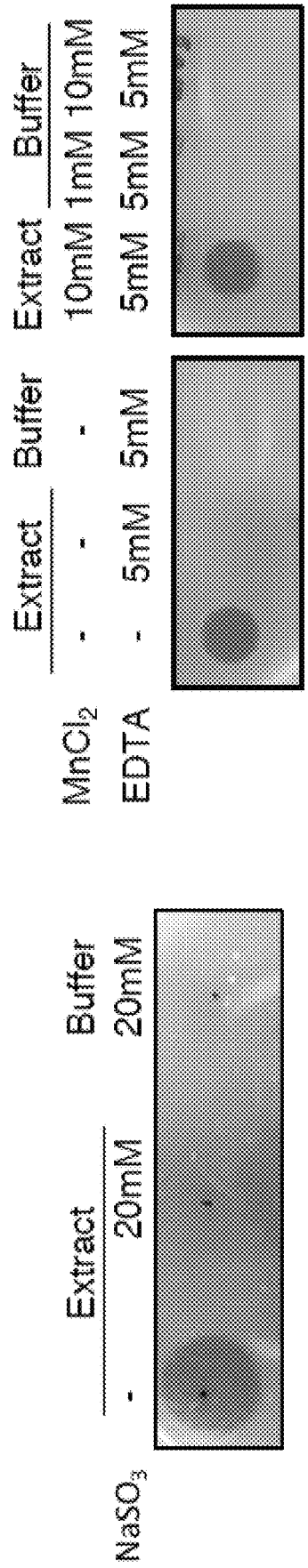
FIG. 6D
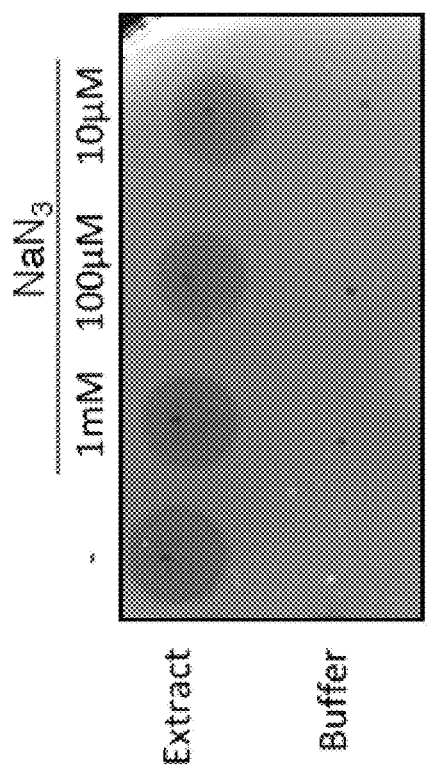
FIG. 6A
FIG. 6C

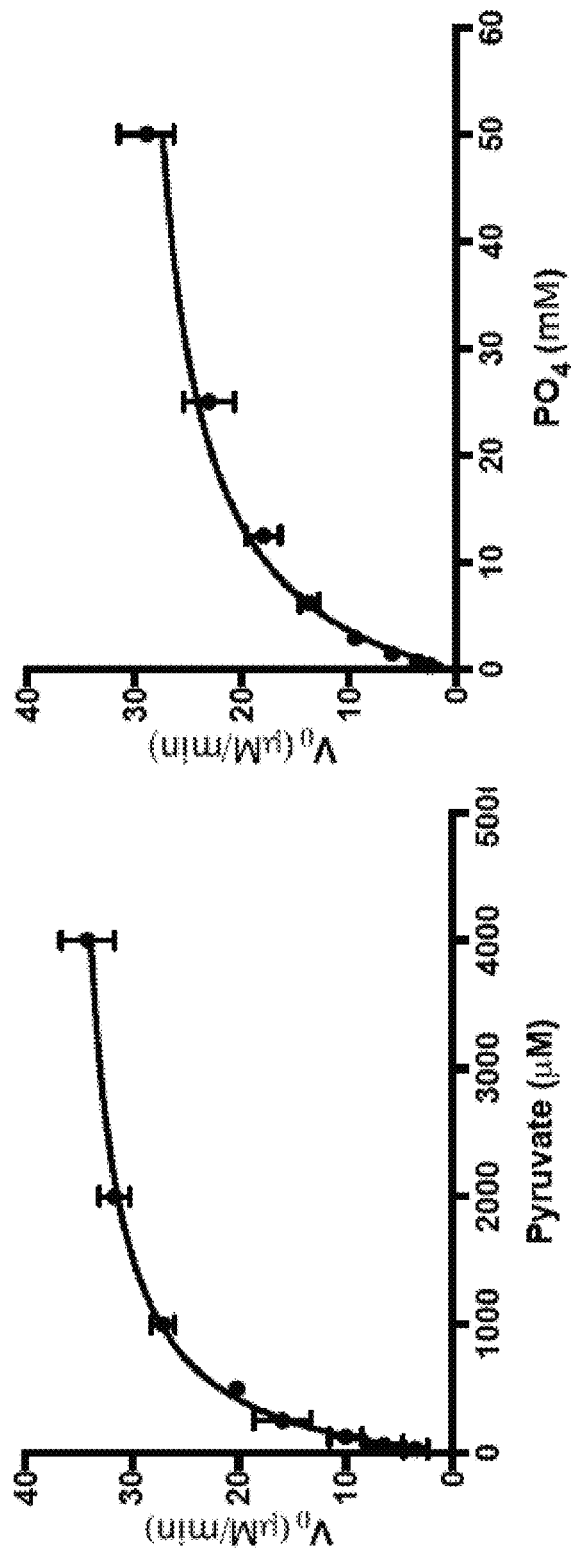
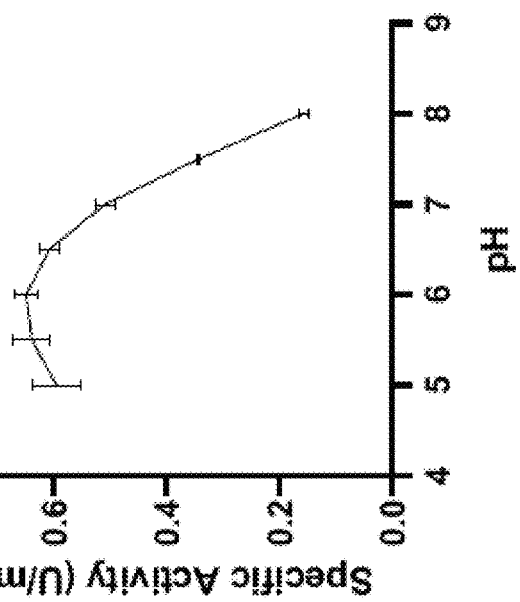
FIG. 13A
FIG. 13B
FIG. 13C

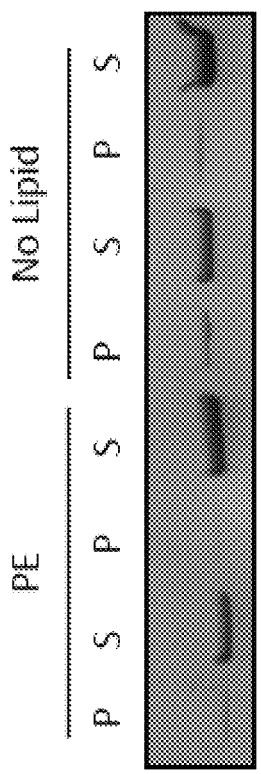
FIG. 17
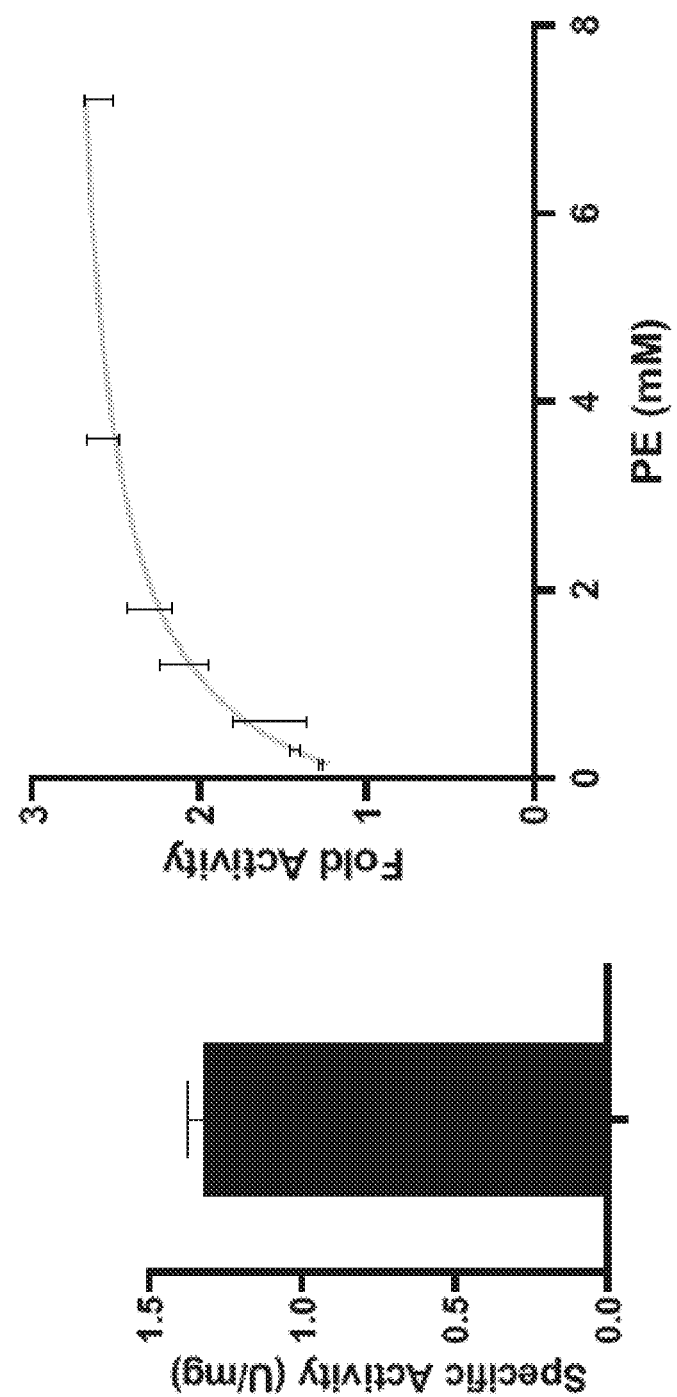
FIG. 18C
FIG. 18B
FIG. 18A

| Gene | Name | Present in non-inhibitor |
|---|---|---|
| LDBND_0093 | Shikimate 5-dehydrogenase | Yes |
| LDBND_0122 | Pyridoxine 5-phosphate oxidase | Yes |
| LDBND_0309 | Multi-copper oxidase | Truncated in non-inhibitors |
| LDBND_1465 | Dihydroorotate oxidase B | Yes |
| LDBND_1487 | Pyruvate oxidase | Truncated in non-inhibitors |
| LDBDN_1877 | Lactate oxidase | Truncated in non-inhibitors |
| LDBND_1905 | NADH-dependent flavin reductase | Yes |
| LDBND_1906 | NADH-dependent flavin reductase | Yes |
| LDBND_2051 | Pyruvate oxidase | Yes |

FIG. 19A

| Enzyme | Reaction | Cofactors | Inhibitors |
|---|---|---|---|
| Pyruvate Oxidase | Pyruvate + $PO_4$ + $O_2$ -> Acetylphosphate + $CO_2$ + $H_2O_2$ | TPP, FAD, $Mn^{+2}$ | $NaSO_3$ |
| Lactate Oxidase | Lactate + $O_2$ -> Pyruvate + $H_2O_2$ | TPP, FAD | Oxalate, $NaSO_3$ |
| Multicopper Oxidase | | $Cu^{+2}$ | $NaN_3$ |

FIG. 19B

| Bacterial strain or plasmid | Description or purpose[a] |
|---|---|
| Strains | |
| *P. gingivalis* | |
| W83 | Clinical isolate, also known as ATCC BAA-308 |
| Tn-FeoB2 | W83 background *feoB2*(PG1294) transposon mutant; Erm[r] |
| Tn-FeoB2 Comp | Complemented Tn-FeoB2 with pT-COW_FeoB2; Erm[r] Tet[r] |
| Tn-FeoB2 Empty | Complemented Tn-FeoB2 with pT-COW; Erm[r] Tet[r] |
| *L. delbrueckii* | |
| STYM1 | Wild-type inhibitor strain isolated from Stonyfield Greek yogurt |
| GVKM1 | Wild-type inhibitor strain isolated from Green Valley Farm kefir |
| SYB7 | Wild-type noninhibitor strain isolated from Smith Family Farm, ME raw milk |
| SYB13 | Wild-type noninhibitor strain isolated from Smith Family Farm, ME raw milk |
| ATCC 11842 | ATCC type strain |
| *S. sanguinis* | |
| SK36 | Wild type |
| *E. coli* | |
| Top10 | Cloning and plasmid maintenance |
| S17-1λpir | Conjugation into *P. gingivalis* |
| DH5α | Cloning and plasmid maintenance |
| LOBSTR | Low background strain for protein expression/purification |
| Plasmids | |
| pT-COW | Complementation vector without insert; Tet[r] Amp[r] |
| pT-COW_FeoB2 | pT-COW with wild-type W83 *feoB2* and promoter |
| pFLAG-CTC_1487-Pox | *E. coli* expression plasmid with His$_6$-tagged pyruvate oxidase (LDBND_1487); Amp[r] |
| pFLAG-CTC_2051-Pox | *E. coli* expression plasmid with His$_6$-tagged pyruvate oxidase (LDBND_2051); Amp[r] |

[a]Erm[r], erythromycin resistance; Tet[r], tetracycline resistance; Amp[r], ampicillin resistance.

FIG. 20

| Primer | Description or purpose | Sequence (5'-3') | SEQ ID NOS: 1-15 |
|---|---|---|---|
| pSAM_WH2_seq1 | Semirandom PCR first round | CCATTGGGAATAATAACCTTTATACCTG | |
| Arb1 | Semirandom PCR first round | GGCCACGCGTCGACTAGTACN10TACNG | |
| pSAM_WH2_seq2 | Semirandom PCR second round | GGTCTCTGCAATTGCTCGAG | |
| Arb2 | Semirandom PCR second round | GGCCACGCGTCACTAGTAC | |
| pSAM_WH2_seq3 | Sequencing of semi-random PCR products | CAAGCAGAAGACGGCATACG | |
| FeoB2_F_NheI | Amplification of W83 feoB2 and promoter region | GACCATGCTAGCTCTTTGCCCAGAGCTGATTC | |
| FeoB2_R_SphI | Amplification of W83 feoB2 and promoter region | GACCATGCATGCTCAGAAGAAAAGTATTCTATCCGGTAG | |
| LDBND_1487_F_RT | qRT-PCR of LDBND_1487 pox | CTGGATGACCCAGAATTCGTGAAG | |
| LDBND_1487_R_RT | qRT-PCR of LDBND_1487 pox | GAAGTTGCTTGAACTTGCAATGCTTC | |
| LDBND_2051_F_RT | qRT-PCR of LDBND_2051 pox | GTTCCCAGTGGGTCTTTTGAC | |
| LDBND_2051_R_RT | qRT-PCR of LDBND_2051 pox | CCATGCAGACACCAAGCTTG | |
| 1487_pox_F_NdeI | Cloning of 1487-pox into pFLAG-CTC | AGATATCATATGGCAAAATTAAGGGCGCAAAC | |
| 1487_pox_R_XhoI | Cloning of 1487-pox into pFLAG-CTC, includes His₆ tag and stop codon | AATTCCCTCGAGTTAGTAGTGATGGTGATGGTGATGACTTCCGTGAG AAGCACCTGAAGTAGTGTC | |
| 2051_pox_F_NdeI | Cloning of 2051-pox into pFLAG-CTC | AGATATCATATGGCAAAATTAAGGGCGCAAACGCT | |
| 2051_pox_R_XhoI | Cloning of 2051-pox into pFLAG-CTC, included His₆ tag and stop codon | AATTCCCTCGAGTTAGTGATGGTGATGGTGATGACTTCCGTGAG AAGCACCTGAAC | |

FIG. 21

| $K_m$ Pyruvate | $K_m PO_4$ | $K_{cat}$ |
|---|---|---|
| 342.2 µM ± 44.9 | 8mM ± 1.35 | 0.367 s$^{-1}$ ± 0.013 |

FIG. 22

| $K_m$ Pyruvate | $K_m PO_4$ | $K_{cat}$ |
|---|---|---|
| 519.9 µM ± 31.85 | 1.25mM ± 0.1336 | 6.85 s$^{-1}$ ± 0.12 |

FIG. 23

| Primer | Description or purpose | Sequence | SEQ ID NOs: 16-17 |
|---|---|---|---|
| Pox_F_NdeI | Cloning of Δ32pox into pFLAG-CTC | AGATATCATATGGCAAAAATTAAGGGCGCAAAC | |
| Pox_R_Δ32_XhoI | Cloning of Δ32pox into pFLAG-CTC, includes His6-tag and stop codon | AATTCCCTCGAGTTAGTGATGATGATGATGATGGTGATGGTGATGACTTCCTGCACCTGAAGCCGGGTCAATTTC | |

FIG. 24

STRAINS OF *LACTOBACILLUS DELBRUECKII* WHICH INHIBIT *PORPHYROMONAS GINGIVALIS*

RELATED APPLICATIONS

This application is a national stage filing under 35 U.S.C. 371 of International Application No. PCT/US2020/023454, filed Mar. 18, 2020, which claims the benefit of U.S. Provisional Application No. 62/820,210, filed Mar. 18, 2019, and U.S. Provisional Application No. 62/837,690, filed Apr. 23, 2019. The entire teachings of the above applications are incorporated herein by reference. International Application No. PCT/US2020/023454 was published under PCT Article 21(2) in English.

GOVERNMENT SUPPORT

This invention was made with government support under Grant Nos. DE024308 and DE025523 awarded by the National Institutes of Health. The government has certain rights in the invention.

STATEMENT REGARDING SEQUENCE LISTING

A Sequence Listing associated with this application is provided in text format in lieu of a paper copy and is hereby incorporated by reference into the specification. The name of the text file containing the Sequence Listing is TFTS-202-301 Sequence Listing 4871-2767-0539v1.txt. The text file is 8 KB, was created on Jan. 25, 2022, and is being submitted electronically via EFS-Web, concurrent with the filing of the specification.

BACKGROUND OF THE INVENTION

Despite improving attitudes toward oral health, periodontal disease remains a prevalent problem and accrues significant ancillary economic costs beyond the immediate health risks. In 2015, the combined treatment costs and productivity lost due to server periodontitis and associated tooth loss is estimated to be a combined $164 billion globally and $44 billion in North America alone. The incidence of some degree of periodontal disease in the United States rises to over 60% of the population over the age of 60. The current therapy for disease is called scaling and root planing which is intended to remove subgingival plaque and smooth the tooth root surface to promote reattachment of the gums. The treatment is painful and often requires extensive home care compliance and follow up visits. Additionally, scaling and root planing is not a preventative treatment option and is thus less cost effective. Antibiotics are occasionally prescribed for treatment, but this is an undesirable treatment option in the age of antibiotic resistance and increasing understanding of the effects of broad-spectrum antibiotics on human microbiota. Research focused on new preventative therapies has the potential to greatly impact oral health and the economics of care for periodontal disease.

SUMMARY OF THE INVENTION

Despite a growing interest in using probiotic microorganisms to prevent disease, very little is understood about the mechanisms by which probiotics exert their action. *Porphyromonas gingivalis* (Pg) is an important pathogen implicated in the development of periodontitis. Several strains of *Lactobacillus delbrueckii* have been isolated from dairy products and examined as described herein for their ability to inhibit Pg growth in vitro. Strain specific inhibition of Pg growth was observed in vitro. Whole genome sequencing of inhibitory and non-inhibitory strains of *L. delbrueckii* revealed significant genetic differences supporting the strain specificity of the interaction. Extracts of the STYM1 *L. delbrueckii* inhibitory strain exhibit inhibitory activity that is abolished by treatment with heat, proteinase K, catalase, and sodium sulfite. The native inhibitory protein(s) were partially purified from *L. delbrueckii* extracts using ammonium sulfate precipitation, anion exchange chromatography, and gel filtration chromatography and identified pyruvate oxidase as the most enriched oxidase present. Addition of pyruvate oxidase substrates and cofactors to STYM1 extracts enhances the production of hydrogen peroxide. Lastly, it is shown herein that purified catalytically active recombinant pyruvate oxidase is sufficient to inhibit Pg growth in vitro without the addition of cofactors. The results underscore the importance of strain selection, not simply species selection, in understanding microbial interactions. Specific *L. delbrueckii* strains or their products can be effective in the treatment and prevention of Pg-associated periodontal disease.

Disclosed herein are methods of treating periodontal disease in a subject. The methods may comprise administering a bacterial strain expressing a STYM1 pox gene product to the subject.

In some embodiments, the bacterial strain is *Lactobacillus delbrueckii*. In some embodiments, the bacterial strain is engineered to overexpress the STYM1 pox gene product. In some embodiments, the bacterial strain is an engineered bacterial strain, such as a *Streptococcus* bacterial strain or a *Corynebacterium* bacterial strain. In some embodiments, the *Streptococcus* bacterial strain is selected from the group consisting of *Streptococcus sanguinis*, *Streptococcus gordonii*, *Streptococcus oralis*, *Streptococcus mitis*, *Streptococcus infantis*, *Streptococcus parasanguinis*, *Streptococcus australis*, *Streptococcus cristatus*, *Streptococcus intermedius*, *Streptococcus salivarius*, *Streptococcus peroris*, *Streptococcus constellatus*, *Streptococcus ratti*, and *Streptococcus sobrinus*. In some embodiments, the *Corynebacterium* bacterial strain is selected from the group consisting of *Corynebacterium matruchotii* and *Corynebacterium durum*.

In some embodiments, the STYM1 pox gene is LDBND_1487. In some embodiments, the bacterial strain inhibits growth of *Porphyromonas gingivalis*. In some embodiments, the bacterial strain produces amounts of hydrogen peroxide inhibitor to *Porphyromonas gingivalis*, thereby treating the periodontal disease in the subject. In some embodiments, administration of the bacterial strain to the subject corrects dysbiosis of the oral microbiota.

In some embodiments, the STYM1 pox gene product is activated by a phospholipid. In some embodiments, the STYM1 pox gene product is activated by phosphotidylethanolamine.

Also disclosed herein is an engineered bacterial strain comprising a STYM1 pox gene.

In some embodiments, the bacterial strain is a *Lactobacillus* bacterial strain, a *Streptococcus* bacterial strain, or a *Corynebacterium* bacterial strain. In some embodiments, the *Lactobacillus* bacterial strain is *Lactobacillus delbrueckii*. In some embodiments, the *Lactobacillus delbrueckii* bacterial strain is engineered to overexpress a STYM1 pox gene product. In some embodiments, the *Streptococcus* bacterial strain is selected from the group consisting of *Streptococcus sanguinis*, *Streptococcus gordonii*, *Streptococcus oralis*,

*Streptococcus mitis, Streptococcus infantis, Streptococcus parasanguinis, Streptococcus australis, Streptococcus cristatus, Streptococcus intermedius, Streptococcus salivarius, Streptococcus peroris, Streptococcus constellatus, Streptococcus ratti*, and *Streptococcus sobrinus*. In some embodiments, the *Corynebacterium* bacterial strain is selected from the group consisting of *Corynebacterium matruchotii* and *Corynebacterium durum*.

In some embodiments, the STYM1 pox gene is LDBND_1487. In some embodiments, the bacterial strain inhibits growth of *Porphyromonas gingivalis*. In some embodiments, the bacterial strain produces amounts of hydrogen peroxide inhibitor to *Porphyromonas gingivalis*.

Also disclosed herein a pharmaceutical composition comprising the engineered bacterial strain described herein.

Disclosed herein are methods of treating periodontal disease in a subject. The methods may comprise administering an engineered bacterial strain expressing a STYM1 LDBND_1487 pox gene product to the subject, wherein the bacterial strain is a *Streptococcus* bacterial strain or a *Corynebacterium* bacterial strain.

Also disclosed herein are engineered bacterial strains. The engineered bacterial strains may comprise a STYM1 LDBND_1487 pox gene, wherein the bacterial strain is a *Streptococcus* bacterial strain or a *Corynebacterium* bacterial strain.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1A shows agar overlay assay with different strains of *L. delbrueckii*. *L. delbrueckii* strains were spotted and allowed to grow for 2 days anaerobically. The plates were moved to an aerobic environment, where the strains were killed by exposure to chloroform vapors and then overlaid with a soft agar inoculated with *P. gingivalis*, incubated, and imaged. FIG. 1B shows spot assay with different strains of *L. delbrueckii*. *L. delbrueckii* strains were spotted and allowed to grow for 2 days anaerobically. The plates were moved to an aerobic environment, where *P. gingivalis* was spotted adjacent to the *L. delbrueckii* spots, allowed to dry, and incubated for 2 days anaerobically. Plates were imaged after the final 2 days of growth.

FIG. 2A shows agar overlay assay with equal protein amounts of soluble cell extracts from STYM1, SYB13, SYB7, and 11842. FIGS. 2B-2E show agar overlay assay with STYM1 cellular extract either treated with Proteinase K (Prot K) or heat-killed Proteinase K (Heat-killed Prot K) (FIG. 2B), passage through a 10 kDa MWCO filter (Flow and Conc.) (FIG. 2C), heat treatment (95° C. for 20 min) (FIG. 2D), or with 10 µg catalase (FIG. 2E).

FIG. 3A shows traces of the absorbance at 280 nm of the eluate of gel filtration of pooled inhibitory fractions from anion exchange chromatography. Fractions were collected starting at 10 mL in 500 µL volumes. FIG. 3B shows agar overlay of gel filtration fractions 7 through 12 from panel A. Fractions were spotted onto plates, allowed to dry under aerobic conditions, and overlaid with a soft top agar inoculated with *P. gingivalis*. Plates were imaged 2 days after anaerobic growth. FIG. 3C provides coomassie stain of gel filtration fractions 7 through 13 after separation by SDS-PAGE. The 70 kDa band from fraction 9 was excised for mass spectrometry analysis.

FIG. 4A shows unique transposon insertion locations for the transposon mutants isolated after exposure to STYM1 cellular extracts are indicated by blue arrows. Only unique insertion sites are marked since some of the isolated mutants had the same insertion sites. FIG. 4B provides confirmation of feoB2 transposon mutant resistance phenotype. The number of CFU after 3 hr exposure to STYM1 extract is shown for the wild type W83 parental strain, the transposon mutant in feoB2 (Tn-FeoB2), the Tn-FeoB2 strain complemented with the wild-type feoB2 gene (Tn-FeoB2 Comp), and the Tn-FeoB2 strain complemented with the empty pT-Cow vector (Tn-FeoB2 Empty). Data represent the average of three independent experiments and error bars represent the standard error. Statistical significance was determined by one-way ANOVA (***, $p<0.001$).

FIG. 5A shows Prussian blue agar plate with 50 µL of known concentrations of $H_2O_2$ in 6 mm diameter wells after incubation at room temperature. FIG. 5B shows Prussian blue agar plate with STYM1 cellular extract alone or supplemented with Pox substrate, Pox substrate plus cofactors, or Lox substrate plus cofactors. Also included as negative controls are the 11842 strain cellular extract and no extract controls with the indicated substrates or cofactors. Images are representative of three independent experiments. FIG. 5C provides a table summarizing diameters of Prussian blue halos. The average diameter of the Prussian blue dye for each condition plus or minus the standard error about the mean. The data represent the average of three independent experiments.

FIGS. 6A-6D demonstrate treatment of STYM1 extracts with oxidase inhibitors. Extract was spotted onto plates, allowed to dry under aerobic conditions, and overlaid with a soft top agar inoculated with *P. gingivalis*. Plates were imaged 2 days after anaerobic growth. STYM1 extract was treated with the indicated concentration of either sodium azide (FIG. 6A), sodium oxalate (FIG. 6B), sodium sulfite (FIG. 6C), or EDTA (FIG. 6D) and tested in an agar overlay assay. Note: In FIG. 6D supplementation with $MnCl_2$ was also included. Black dots indicate where the extract was added to the surface of the plate.

FIG. 7A provides alignment of the C-terminal region of LDBND_1487 Pox and LDBND_2051 Pox. The preceding N-terminal region is identical. FIG. 7B provides alignment of the promoter regions of LDBND_1487 and LDBND_2051 with predicted −35 and −10 sites and the ribosome binding site, and the start codon indicated. FIG. 7C shows the expression of levels of the two pyruvate oxidase genes in STYM1 at the time of cellular extract harvest were measured by qRT-PCR. The graphs represent the mean expression level of LDBND_2051 relative to LDBND_1487 within each sample. The expression of LDBND_1487 was set to one in each sample. The data represent three independent experiments and error bars represent standard error about the mean. Statistical significance was determined by a two-tailed t-test (**, p<0.01).

FIG. 8A provides Coomassie stain of fractions from Ni-NTA purification of LDBND_1487 Pox: flow through (FT), Wash 1 (W1), Wash 2 (W2), Elution 1 (E1), and Elution 2 (E2) (left blot), as well as Coomassie stain of purified Pox after SDS-PAGE (middle blot), and Coomassie stain of purified 1487-Pox and 2051-Pox after SDS-PAGE (right blot). FIG. 8B provides a standard curve of $H_2O_2$ concentrations in the pyruvate oxidase activity assay. FIG. 8C shows pyruvate oxidase activity assay with a 1:10 dilution of purified Pox from FIG. 8A. Pyruvate oxidase activity is determined by calculating the change in $A_{550}$ per minute and extrapolating to the standard curve in FIG. 8B. 1 unit of Pox activity is defined as the production of 1 μmol of $H_2O_2$ per minute. FIG. 8D shows agar overlay assay of purified 1487-Pox or 2051-Pox alone or purified 1487-Pox or 2051-Pox supplemented with substrate and/or substrate and cofactors. Buffer controls are also included. Enzyme mixtures were spotted onto plates, allowed to dry under aerobic conditions, and overlaid with a soft top agar inoculated with *P. gingivalis*. Plates were imaged 2 days after anaerobic growth.

FIG. 9A shows *P. gingivalis* end point growth after two days is shown with or without the addition of overnight or 48-hour supernatants from the STYM1 strain grown in BHI. Data represent the mean of three independent experiments and error bars represent one standard error about the mean. Statistical Significance was determined by One-way ANOVA (*** p<0.001) FIG. 9B provides growth curves of the STYM1 strain grown in either BHI or BHI supplemented with 2% glucose under anaerobic conditions. The growth curves represent the average of three independent experiments. Error bars represent the standard error.

FIG. 10A provides gene maps of the pox region in STYM1, SYB7, and 11842. Indicated are the hypothetical membrane protein (orange), pyruvate oxidase (LDBND_1487) (pox, blue), and D-Ala-D-Ala carboxypeptidase (dacA, yellow). FIG. 10B provides gene maps of the lox region in STYM1, SYB7, and 11842. Indicated are the oligopeptidase F (pepF, red), lactate oxidase (lox, blue), lactate permease (lctP, green), zinc ribbon protein (dark purple), and an Mn/Zn permease (light purple). FIG. 10C provides gene maps of the Imo region in STYM1, SYB7, and 11842. Indicated are the peptide release factor C (prfC, aqua), hypothetical proteins (orange), multi-copper oxidase (Imo, green), and ClpE protease (clpE, red).

FIGS. 13A-13C demonstrate kinetic parameters of *L. delbrueckii* Pox. FIG. 13A shows enzyme velocity of *L. delbrueckii* Pox at various concentrations of pyruvate in the reaction mixture. FIG. 13B shows enzyme velocity of *L. delbrueckii* Pox at various concentrations of Phosphate in the reaction mixture. In both panels, enzyme concentration was 1.76 uM. The data represent the average of two independent experiments and error bars represent standard error. FIG. 13C shows enzyme specific activity at various pHs. The data represent the average of two independent experiments and error bars represent standard error.

FIG. 14A provides size exclusion chromatography of *L. delbrueckii* Pox. 840 ug of Pox was combined with 50 mM pyruvate, 300 uM TPP, and 15 uM FAD and applied to the column. The absorbance at 280 nm is shown along with the elution position of known protein standards indicated by arrows. The calculated weight of the *L. delbrueckii* Pox is indicated based on the standard curve. 1 mL fractions were collected beginning at 10 mL elution volume to the end of the elution. FIG. 14B provides a standard curve of gel filtration elution volumes for known protein standards. FIG. 14C provides a Coomassie stain of indicated fractions from gel filtration after SDS-PAGE under non-reducing conditions. FIG. 14D provides a Coomassie stain of purified *L. delbrueckii* Pox after SDS-PAGE under reducing (5% beta-mercaptoethanol) and non-reducing conditions.

FIG. 15A shows the fold activity of *L. delbrueckii* Pox relative to the enzyme activity with no added phospholipid with various concentrations of phosphotidylethanolamine (16:0-18:1) (PE), phosphotidylcholine (16:0-18:1) (PC), and phosphotidylglycerol (16:0-18:1) (PG). Data represent the average of two independent experiments and error bars represent the standard error. FIG. 15B shows the fold activity of *L. delbrueckii* Pox with various concentrations of PE relative to enzyme activity with no PE. Data represent the average of at least two independent experiments and error bars represent the standard error.

FIG. 16A shows the enzyme velocity of *L. delbrueckii* Pox at various concentrations of pyruvate in the reaction mixture with 7.2 mM PE. FIG. 16B shows the enzyme velocity of *L. delbrueckii* Pox at various concentrations of phosphate in the reaction mixture with 7.2 mM PE. In both panels, enzyme concentration was 170 nM. The data represent the average of two independent experiments and error bars represent standard error.

FIG. 17 demonstrates L. delbrueckii does not co-precipitate with PE. L. delbrueckii Pox with 50 mM pyruvate, 300 uM TPP, and 15 uM FAD was incubated with 1 mM PE or no lipid. The lipid fraction was pelleted by centrifugation after 30 minutes. Shown is a Coomassie stain of either the lipid pellet fraction (P) or the soluble fraction (S).

FIGS. 18A-18C demonstrate that the C-terminal 32 amino acids are important for lipid activation. FIG. 18A provides a Coomassie stain of purified Δ32 Pox enzyme. FIG. 18B shows specific activity of the purified Δ32 Pox enzyme. Data represent the average of two independent experiments and the error bar represent standard error. FIG. 18C shows the fold activity of Δ32 Pox enzyme with various concentrations of PE relative to enzyme activity with no PE. Data represent the average of two independent experiments and error bars represent the standard error.

FIGS. 19A-19B show three oxidases are uniquely present in the STYM1 strain of L. delbrueckii. FIG. 19A provides a table identifying oxidases in STYM1. The gene number and name of oxidases in STYM1 are listed. Also indicated is whether the oxidase is present in non-inhibitor strains. FIG. 19B provides a table identifying properties of unique STYM1 oxidases.

FIG. 20 provides a table summarizing the bacterial strains and plasmids used herein.

FIG. 21 provides a table summarizing the primers used in Example 1 described herein.

FIG. 22 provides a table summarizing kinetic parameters of L. delbrueckii Pox. Values for each parameter are listed with standard error.

FIG. 23 provides a table summarizing kinetic parameters of L. delbrueckii Pox with PE. Values for each parameter are listed with standard error.

FIG. 24 provides a table summarizing primers used in Example 2 described herein.

DETAILED DESCRIPTION OF THE INVENTION

Figures 1A, 1B:
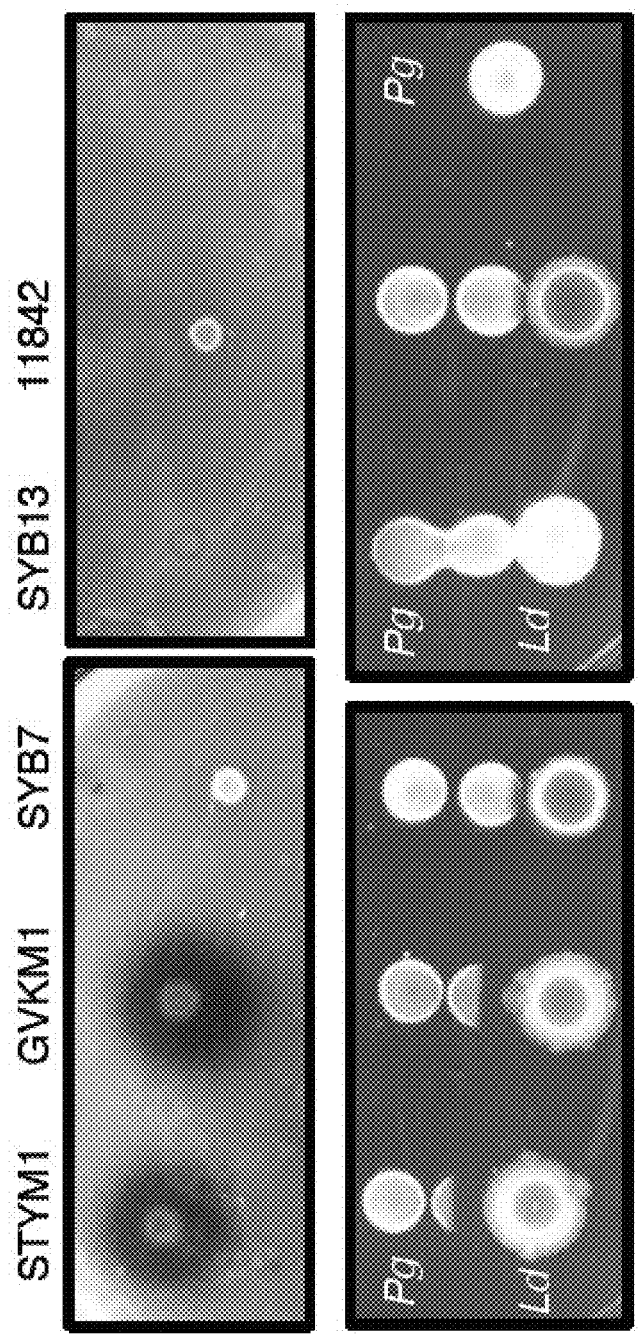
FIGS. 1A-1B demonstrate *L. delbrueckii* inhibition of *P. gingivalis* is strain specific.

Porphyromonas gingivalis is implicated in the onset and progression of periodontal disease and associated with some systemic diseases. Probiotic bacteria represent an attractive preventative therapy for periodontal disease. However, the efficacy of probiotic bacteria can be variable between studies. The data presented herein supports the known importance of selecting particular strains of bacteria for probiotic use, not simply a single species. Specifically, in the context of probiotic intervention of periodontitis, the data suggests that high-level expression of pyruvate oxidase with hydrogen peroxide production in Lactobacillus delbrueckii could be an important characteristic for the design of a probiotic supplement or a microbial therapeutic.

Disclosed herein are methods of treating periodontal disease in a subject by administering to the subject a bacterial strain that expresses a pyruvate oxidase (pox) gene product. In some aspects, the bacterial strain is a L. delbrueckii bacterial strain. For example, the L. delbrueckii bacterial strain may be STYM1 or GVKM1, both of which are isolated from yogurt products. In some aspects, the L. delbrueckii bacterial strain is isolated from raw milk. In certain embodiments, the L. delbrueckii bacterial strain is STYM1.

In some embodiments an extract of STYM1 or GVKM1 produces hydrogen peroxide. Hydrogen peroxide may be produced by pyruvate oxidase (pox), lactate oxidase (lox), or multicopper oxidase (mco), all genes present in STYM1. In some aspects hydrogen peroxide exerts antimicrobial effects, and therefore hydrogen peroxide production is likely a function of an inhibitory protein in STYM1 extracts. In certain embodiments, pox is the primary hydrogen peroxide-producing enzyme in STYM1 extracts. In some embodiments STYM1 encodes for two predicted pox genes. In certain aspects STYM1 encodes for LDBND_1487 and LDBND_2051. In certain embodiments, STYM1 encodes for LDBND_1487.

In some embodiments, the pox enzyme is activated (e.g., catalytically activated) by lipids, e.g., phospholipids. k certain embodiments, a hydrogen-peroxide producing Pox from L. delbrueckii strain STYMI is activated by a phospholipid (e.g., phosphotidylethanolamine).

Described herein is a specific strain of L. delbrueckii that treats periodontal disease, such as by inhibiting the growth of P. gingivalis, by producing inhibitory concentrations of hydrogen peroxide primarily through a pyruvate oxidase (pox) enzyme. The specific strain of L. delbrueckii was isolated from yogurt (e.g., Stonyfield Greek yogurt), and the strain is unmodified from its original isolation state. However, the purified recombinant pyruvate oxidase from this strain is capable of inhibiting P. gingivalis on its own. In some embodiments, the specific bacterial strain is engineered to overexpress the STYM1 pox gene product. In some embodiments, the STYM1 pox gene is LDBND_1487.

The oral cavity is not the natural niche for L. delbrueckii. Therefore, it may be desirable to engineer strains that better colonize the tooth surface and oral cavity to express the LDBND_1487 Pox enzyme. Thus, also disclosed herein are bacterial strains engineered to express a Pox enzyme (e.g., LDBND_1487 Pox). Bacterial strains which do not natively produce the enzyme may be genetically engineered to produce the enzyme, or a bacterial strain that natively/endogenously expresses the enzyme may be genetically engineered to produce increased amounts of the enzyme compared with corresponding native strains, optionally along with other enzymes to increase the ability of the strain to colonize the oral cavity. For example, an isolated cell (e.g., a bacterial cell) may be transfected with a plasmid comprising a polynucleotide encoding the enzyme or functional portion thereof. Preferably the cell will be one which does not naturally produce the enzyme. However in certain embodiments the cell naturally expresses the enzyme and the genetic modification results in overproduction of the enzyme. Following the integration and expression of such nucleic acids into the genome of the isolated cell, such cell will produce or express the Pox enzyme (e.g., the LDBND_1487 Pox enzyme).

Any bacterial strain suitable for colonizing a tooth surface and/or oral cavity may be used. For example, it is possible to engineer streptococci that are normal colonizers of the oral cavity. These include but are not limited to: Streptococcus sanguinis, Streptococcus gordonii, Streptococcus oralis, Streptococcus mitis, Streptococcus infantis, Streptococcus parasanguinis, Streptococcus australis, Streptococcus cristatus, Streptococcus intermedius, Streptococcus salivarius, Streptococcus peroris, Streptococcus constellatus, Streptococcus ratti, and Streptococcus sobrinus.

In some aspects, the LDBND_1487 Pox gene is introduced into the bacterial strain (e.g., a Streptococcus species above) by using either a streptococcal shuttle plasmid such as pDL276 or inserted into the genome via homologous recombination or another means of genetic modification. For use on a streptococcal shuttle plasmid, the LDBND_1487 gene may be ligated into pDL276 or another shuttle vector.

In some aspects, expression of the LDBND_1487 Pox on the vector may be controlled either by the native LDBND_1487 promoter sequence, a constitutively active streptococcal promoter sequence (such as $P_{ami}$, $P_{spac}$, $P_{23}$, $P_{veg}$), or an inducible streptococcal promoter sequence that is responsive to some environmental signal that would ensure that LDBND_1487 pox is expressed at the optimal time and space within the oral cavity.

For insertion into the genome of a *Streptococcus* species, the LDBND_1487 Pox gene may be amplified and subsequently fused to approximately 500-1000 bp pieces of DNA from the genome on both sides of the LDBND_1487 Pox gene via overlap extension PCR. This fragment will include one of the promoter elements described above for use in the shuttle vector approach. Insertion of the fragment will be directed into an intergenic space that does not influence expression of surrounding genes.

There is also evidence that Corynebacteria in the oral cavity associate tightly with *Porphyromonas* species. Thus, it would be advantageous for a *Corynebacterium* to express the LDBND_1487 Pox and produce hydrogen peroxide so that it is produced in close proximity to *Porphyromonas*. The dominant species in the oral cavity that may be used are *Corynebacterium matruchotii* and *Corynebacterium durum*. In some aspects, the LDBND_1487 Pox gene is introduced into the *Corynebacterium* species either with a *Corynebacterium* shuttle vector like pCGL0243 or inserted into the genome via homologous recombination or another means of genetic modification. In some aspects, the expression is controlled by either the native LDBND_1487 promoter sequence, a constitutively active *Corynebacterium* promoter sequence (such as the CP_2454 promoter from *Corynebacterium glutamicum*), or an inducible *Corynebacterium* promoter sequence that is responsive to some environmental signal that would ensure that LDBND_1487 pox is expressed at the optimal time and space within the oral cavity.

Insertion of the LDBND_1487 pox gene into the genome of *Corynebacterium* may be done by incorporating LDBND_1487 pox gene into the suicide vector, pJSC232. Regions of homology to a region in the *Corynebacterium* genome may be included on the vector to enable integration into the genome at an intergenic region. Expression of LDBND_1487 in this system may be controlled by one of the promoter elements described above for *Corynebacterium*.

Periodontitis remains a common disease in which the gingival tissue is chronically inflamed due to a dysbiosis of the oral microbiota. This inflammation can result in tissue destruction, bone loss, and eventual tooth loss. Periodontitis has also been linked to a variety of systemic diseases. Recently, a keystone pathogen in the development of periodontitis, *P. gingivalis*, has been linked to the development of Alzheimer's disease, which has increased the interest in inhibiting *P. gingivalis* growth.

To our knowledge, this is the first strain of *L. delbrueckii* known to inhibit the growth of *P. gingivalis*. To our knowledge, the pyruvate oxidase from *L. delbrueckii* has not been purified and shown to produce inhibitory concentrations of hydrogen peroxide. Using a bacterial strain or recombinant protein has advantages over the current therapies since it can be used preventatively and is not a broad-spectrum antibiotic.

Pyruvate oxidase (Pox) is an important enzyme in bacterial metabolism for increasing ATP production and providing a fitness advantage via hydrogen peroxide production. It also has applications in the development of biosensors for pyruvate and phosphate measurement. The hydrogen-peroxide-producing Pox from *L. delbrueckii* strain STYM1 was characterized and it was shown that it is specifically activated by phosphotidylethanolamine (16:0-18:1). This activation is a mixture of K- and V-type activation as both $k_m$ and enzyme turnover are altered. Furthermore, it was demonstrated that the *L. delbrueckii* Pox forms pentamers and either decamers or dimers of pentamers in solution, which is different from other characterized Pox enzymes. Lastly, a C-terminal truncation mutant was generated that was only weakly activated by phosphotidylethanolamine, which suggests the C-terminus is important for lipid activation. This appears to be the first known hydrogen-peroxide producing Pox enzyme that is activated by phospholipids. The results suggest that there are substantial differences between Pox enzymes from different bacterial species, which could be important for their role in biological systems as well as in the development of Pox-based biosensors.

EXAMPLES

Example 1: Interspecies Inhibition of *Porphyromonas gingivalis* by *Lactobacillus delbrueckii* Require Active Pyruvate Oxidase Periodontitis, an inflammatory disease of the tissue that supports the teeth, is caused by a dysbiosis or imbalance between beneficial and pathogenic oral bacteria (1). This contributes to inflammation and, if left untreated, eventually results in alveolar bone and tooth loss. One of the major bacteria associated with periodontitis is *Porphyromonas gingivalis* (Pg), which is considered to be a keystone pathogen in periodontal disease (1). Current treatment for periodontitis involves intensive and expensive therapies such as scaling and root planning as well as antibiotic treatment which are not preventative treatments.

Probiotics are microorganisms that when administered confer a beneficial effect on the health of an individual (2). Most probiotics research and current applications are focused on bacteria that colonize the intestines and exert their effects from this location. Some of the most well-studied probiotics include *Lactobacillus, Bifidobacterium*, and *Lactococcus* species that colonize the gut and have beneficial effects on celiac disease, obesity, irritable bowel syndrome, *Campylobacter jejuni* infection, and infant sepsis (3-10). Commonly found in yogurts and other fermented foods, *Lactobacillus* species are widely regarded as safe for administration to immune competent individuals (11). Use of probiotic *Lactobacillus* and *Lactococcus* species is just beginning to be explored in the oral cavity (12-15). Several recent studies have examined the efficacy of probiotics in the treatment of dental caries. Many of these studies employed administration of different *Lactobacillus* species by different vehicles (i.e. milk, cheese, yogurt, tablets etc.) for varying time spans. These studies demonstrated a significant decrease in carriage of *Streptococcus mutans* (the predominant bacterium involved in dental caries) and reduced caries risk as well as reduced periodontal disease symptoms following treatment with the probiotic, thereby underscoring the feasibility of probiotic use in the oral cavity (13, 16). Furthermore, a recent study of a Korean cohort established that individuals with increased yogurt consumption, but not milk or calcium, had decreased incidence of periodontitis suggesting the bacteria present in yogurt may be important (17).

In this study, strains of *Lactobacillus delbrueckii* that inhibit the growth of *Porphyromonas gingivalis* were isolated. It was subsequently determined that the mechanism by which this strain of L. delbrueckii exerted its effect was through the enzymic activity of pyruvate oxidase.

Results

Inhibition of Porphyromonas gingivalis by Lactobacillus delbrueckii is Strain Specific Two strains of Lactobacillus delbrueckii (Ld) were isolated from commercial dairy products and two strains from raw milk (ref for basis of isolation). The commercial isolates were STYM1 and GVKM1 while the raw milk isolates were named SYB7 and SYB13. Their identification was confirmed by 16S rRNA sequencing (data not shown). Each of these strains were examined, as well as the ATCC 11842 type strain, for its ability to inhibit Pg growth in an agar overlay assay and a spot assay. Both STYM1 and GVKM1 inhibit Pg growth in both assays while SYB7 and SYB13 isolates and the 11842 strain have little impact on Pg growth (FIG. 1).

Figure 9B:
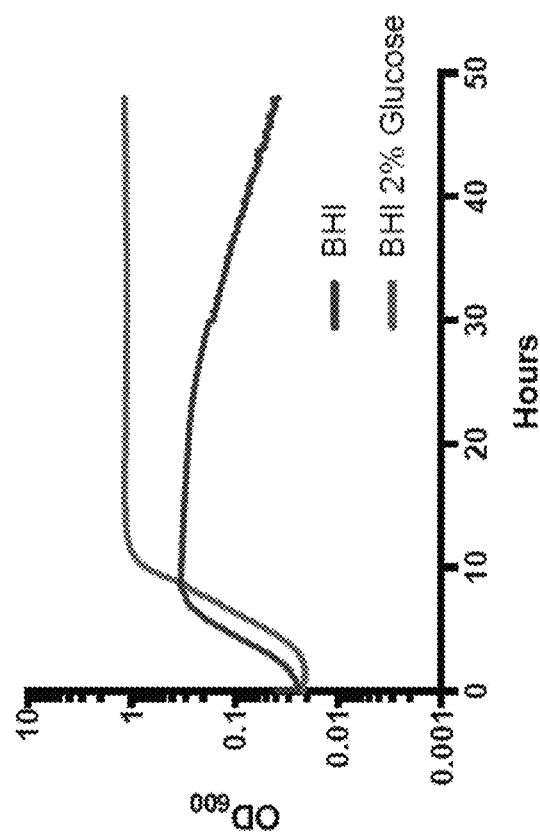
FIGS. 9A-9B demonstrate release of intracellular components into 48-hour supernatant via autolysis of STYM1 inhibits *P. gingivalis*.
Figure 9A:
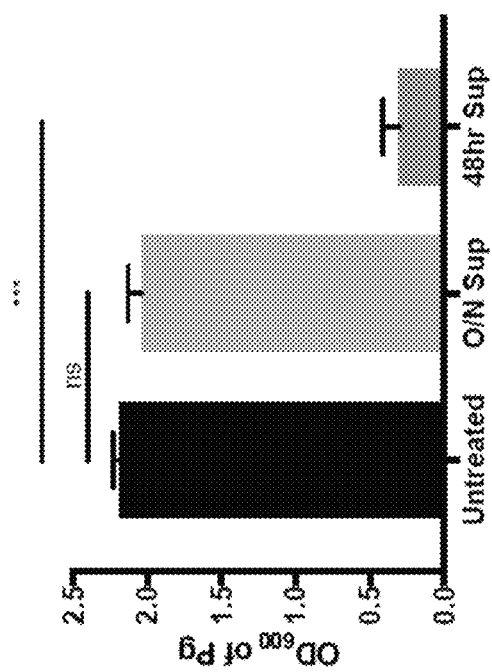

The characterization of the STYM1 strain was focused on since it showed the most inhibition of Pg. Since Lactobacilli are known to secrete antimicrobial molecules, the supernatant from STYM1 grown in brain heart infusion (BHI) broth was tested for whether it had inhibitory activity toward Pg. Cell-free supernatants were harvested from either overnight or 48 hr STYM1 cultures and tested for activity in a broth-based assay monitoring end-point Pg growth. The 48 hr supernatant inhibited growth of Pg to a much greater degree than that of the overnight culture (FIG. 9A). However, when examining the growth dynamics of STYM1 in BHI broth culture, significant autolysis of the STYM1 culture during the period of 24-48 hrs of incubation was observed (FIG. 9B). Previous research has demonstrated that lactobacillus species can undergo autolysis in late stationary phase especially in response to carbon starvation (21, 22). BHI media only contains 0.2% (w/v) glucose so it was tested whether glucose limitation induced autolysis under these conditions. Indeed, it was found that the autolysis of STYM1 in BHI was due to carbon limitation (FIG. 9B). Considering that only the 48 hr culture supernatant had inhibitory activity, it was reasoned that the inhibitory molecule could be an intracellular component released into the supernatant via autolysis.

Cellular Extracts of STYM1 Contain an Inhibitory Protein

Figure 2A:
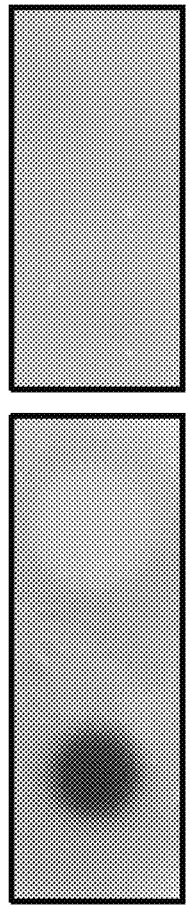
FIGS. 2A-2E demonstrate STYM1 cellular extracts have inhibitory activity. Extract was spotted onto plates, allowed to dry under aerobic conditions, and overlaid with a soft top agar inoculated with *P. gingivalis*. Plates were imaged 2 days after anaerobic growth.
Figure 2C:
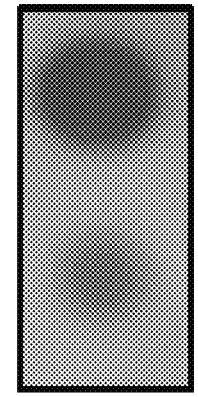
Figure 2E:
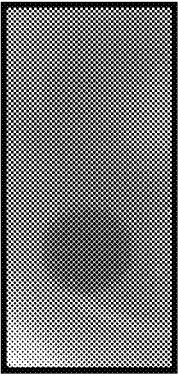
Figure 2B:
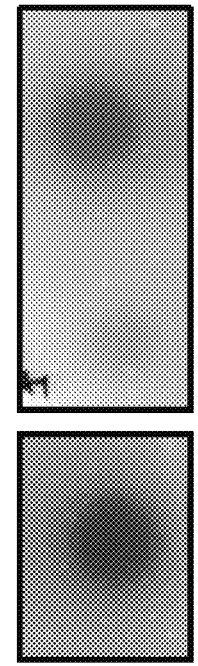
Figure 2D:
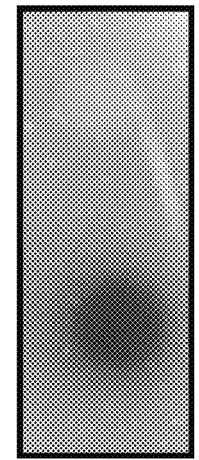

To confirm that the inhibitory molecule is located intracellularly, soluble cellular extract was tested for inhibitory activity in an agar overlay assay. Only the STYM1 cellular extract had inhibitory activity while the extracts from the non-inhibitory strains had no effect on Pg growth (FIG. 2A). To determine the nature of the inhibitory activity in the STYM1 extract, the extract was treated with either heat, proteinase K, or passage through a 10 kDa molecular weight cut-off filter. Treatment with heat and proteinase K completely abolished inhibitory activity in STYM1 extract and the 10 kDa MWCO filter retained the majority of the inhibitory activity suggesting that one or several proteins are responsible for the inhibition of Pg (FIGS. 2B-2D).

Fractionation of STYM1 Extract

Figures 3A, 3B, 3C:
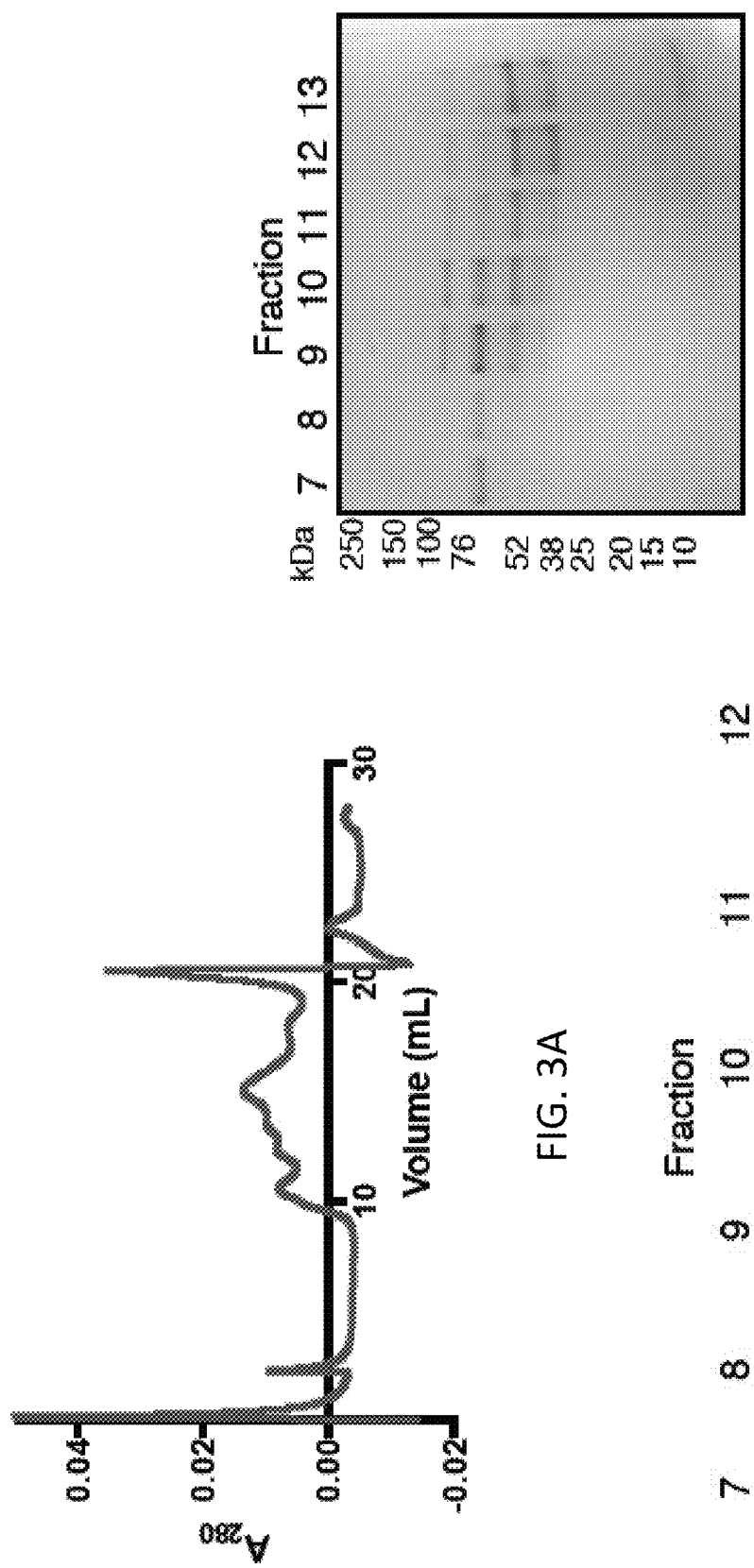
FIGS. 3A-3C demonstrate fractionation of STYM1 cellular extracts.

To identify the inhibitory protein in the STYM1 extracts, the extracts were fractionated using ammonium sulfate precipitation, anion exchange chromatography, and gel filtration. Fractions with inhibitory activity were pooled and used as input for the next fractionation step. After gel filtration, inhibitory activity peaked in fraction 9 (FIGS. 3A-3B). Proteins in this fraction were visualized by coomassie staining after SDS-PAGE, which revealed only three bands with one dominant band at approximately 70 kDa (FIG. 3C). The dominant band at 70 kDa in fraction 9 was excised from the gel and analyzed by mass spectrometry. The top 5 most abundant proteins in the sample were glutamine-fructose-6-phosphate aminotransferase, pyruvate oxidase, pyruvate kinase, phosphoenolpyruvate-protein phosphotransferase, and molecular chaperone DnaK. Interestingly, three of the five enzymes are involved in pyruvate metabolism which may indicate that they form a complex.

Genomic Analysis of Inhibitor Versus Non-Inhibitor Strains

A genomics approach was taken to determine the differences between inhibitor versus non-inhibitor strains of L. delbrueckii and to identify if any proteins by mass spectrometry were unique to inhibitor strains. Whole genome sequencing of two inhibitor strains (STYM1 and GVKM1) and two non-inhibitor strains (SYB7 and ATCC 11842) revealed many differences and genomic rearrangements. The two inhibitor strains were very similar only having 13 variants. However, the STYM1 genome is approximately 400 kb larger than the 11842 genome and SYB7 genome and not surprisingly has 426 additional genes that are unique many of which are transposases, of metabolic function or hypothetical.

Figure 10A:
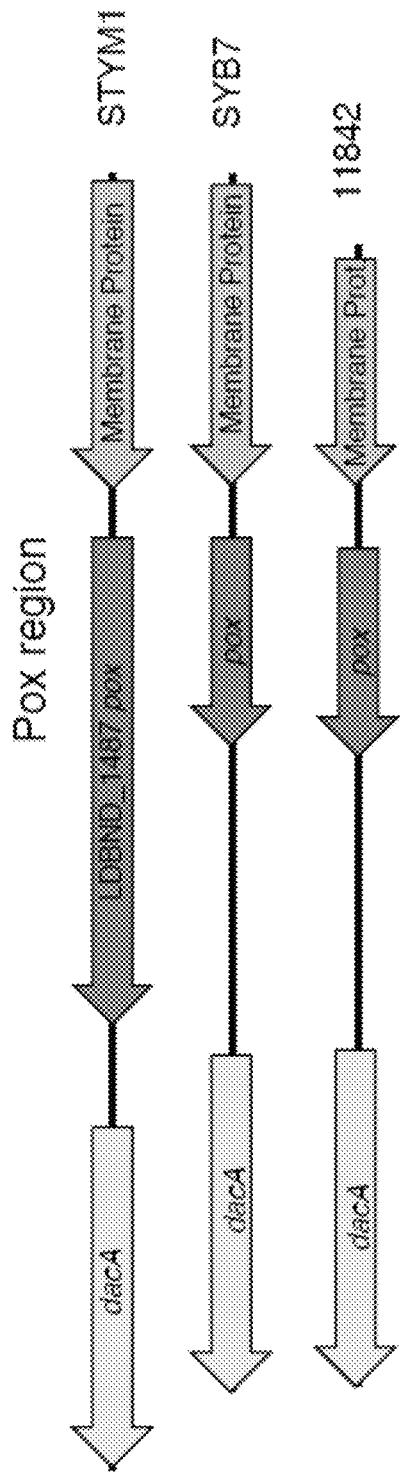
FIGS. 10A-10C demonstrate *L. delbrueckii* genome heterogeneity of pox, lox, and Inco regions.
Figure 10B:
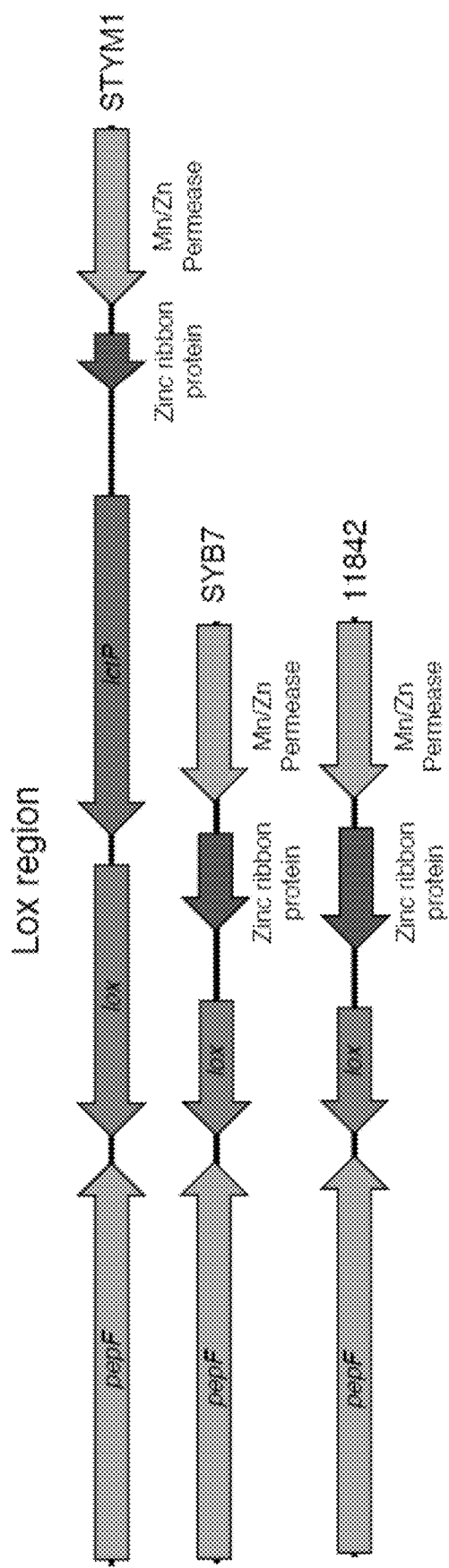
Figure 10C:
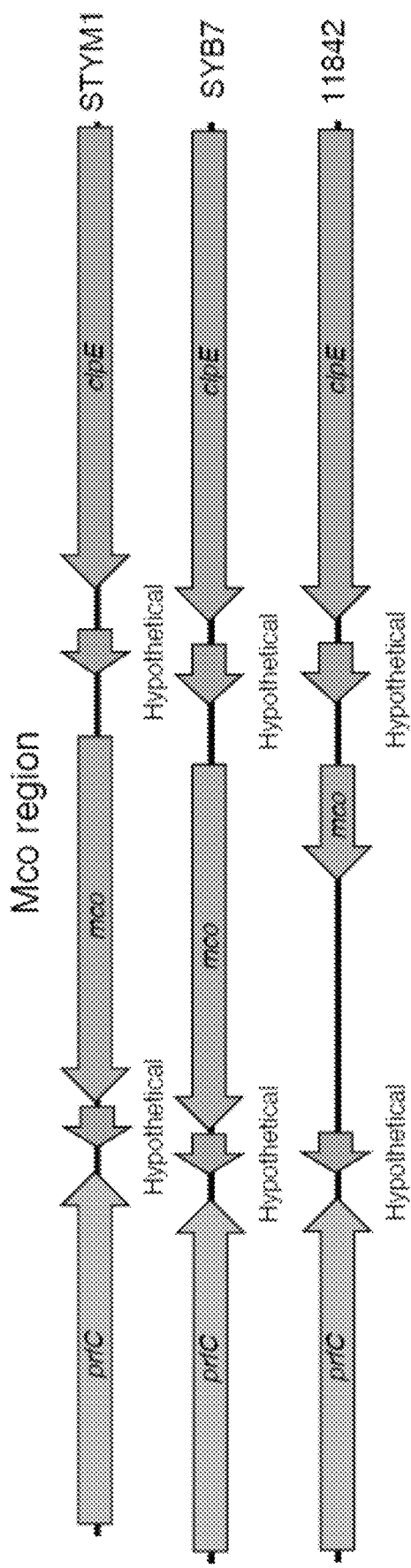

The genome analysis was used to determine if any of the proteins identified by mass spectrometry were unique to the inhibitor strain relative to non-inhibitor strains. This analysis revealed that three oxidase genes identified by mass spectrometry, pyruvate oxidase (Pox), lactate oxidase (Lox), and multicopper oxidase (Mco), are truncated in non-inhibitory strains and likely produce non-functional peptides (FIG. 10). At the pox locus, the genomic arrangement is similar in inhibitor and non-inhibitor strains, but there is a 283 bp deletion within the pox gene in the non-inhibitor strains that results in the introduction of a premature stop codon. In the lox region, the 5' region of lox as well as the entire upstream lactate permease gene are deleted in the non-inhibitor strains. In the multi-copper oxidase region, one inhibitor strain has an intact mco gene, but the 11842 strain has a 7 bp insertion that results in the introduction of a premature stop codon (FIG. 10). Since Pox, Lox, and some multicopper oxidases generate hydrogen peroxide, it was tested whether addition of catalase to STYM1 cellular extracts could eliminate inhibitory activity. Indeed, catalase treatment of STYM1 extracts completely abolished inhibitory activity demonstrating that hydrogen peroxide production, likely by one or more of the oxidases identified by mass spectrometry, is the mechanism of action (FIG. 2E).

Screening of Pg Transposon Library by Exposure to STYM1 Extracts

Figure 4A:
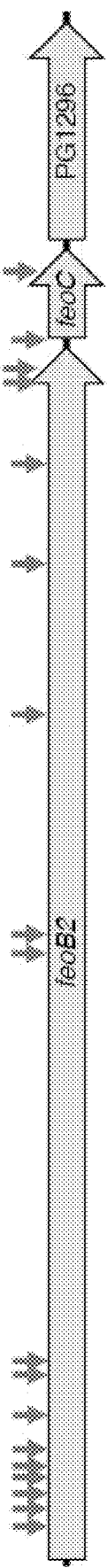
FIGS. 4A-4B demonstrate Transposon insertions in *P. gingivalis* feoB2 operon confer resistance to killing by STYM1 extracts.
Figure 4B:
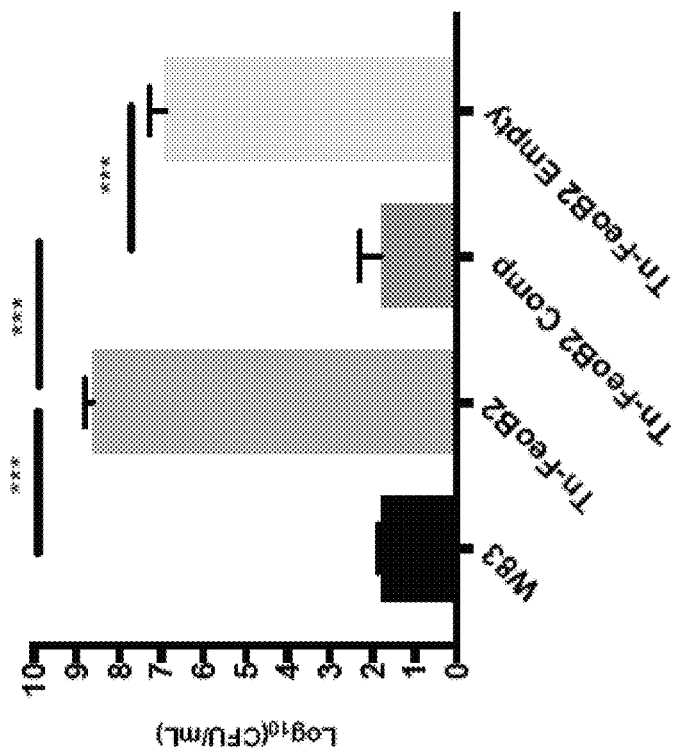

Next, it was determined whether hydrogen peroxide was the major component of STYM1 inhibitory activity and whether Pg resistant mutants could be isolated. To do this, a transposon library constructed in the W83 strain of Pg was used. The Pg transposon library was exposed to STYM1 extract and then plated for survivors. 36 surviving colonies were selected and their transposon:genome junctions were sequenced to determine the location of transposon insertion. Remarkably, 34 of 36 clones had transposon insertions in the feoB2 gene (PG1294) of W83 while the other two clones had transposon insertions in the predicted feoC homologue, FeoB-associated Cysteine-rich membrane protein (FIG. 4A). FeoB2 has been previously characterized as an iron transporter in Pg (23, 24). Deletion mutants of feoB2 have lowered intracellular iron levels, are unable to grow in vivo in a mouse abscess model, and have increased resistance to hydrogen peroxide and atmospheric oxygen (23, 25). When tested in isolation, the feoB2 transposon mutant displays significantly greater resistance to killing by STYM1 extract and complementation with the native feoB2 gene restores sensitivity (FIG. 4B). These data confirm that resistance is due to disruption of the feoB2 gene not the presence of a secondary site mutation elsewhere in the genome or downstream polar effects.

One of the main mechanisms by which hydrogen peroxide exerts antimicrobial effects is through the formation of reactive oxygen species via the Fenton reaction with intracellular iron (26). Because only transposon mutants in feoB2 that were resistant to killing by STYM1 extracts were recovered, it was reasoned that hydrogen peroxide production must be the dominant function of the inhibitory protein in the STYM1 extracts.

Supplementation of STYM1 Extracts with Pox Substrates and Cofactors Enhances $H_2O_2$ Production.

Figure 5A:
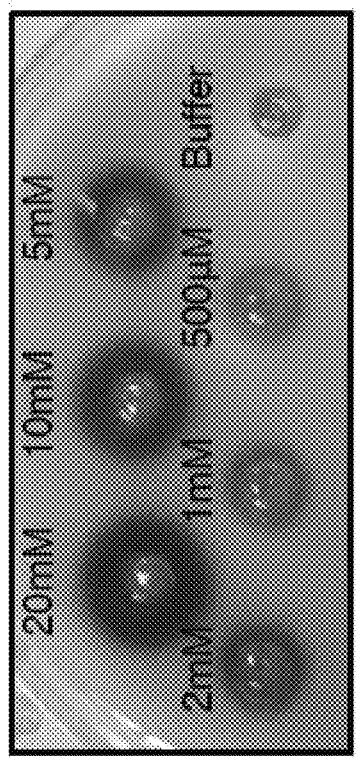
FIGS. 5A-5C demonstrate supplementation of STYM1 extract with Pyruvate oxidase substrates and cofactors enhances $H_2O_2$ production.

In *Lactobacillus* species, Pox catalyzes the conversion of pyruvate, phosphate, and oxygen to acetyl phosphate, carbon dioxide and hydrogen peroxide. Pox employs thiamine pyrophosphate (TPP), flavin adenine dinucleotide (FAD), and $Mn^{+2}$ to carry out this reaction (27, 28). Since Pox was one of the most enriched proteins in the inhibitory fractions after gel filtration, it was determined whether hydrogen peroxide production could be increased in the STYM1 extracts by simply adding substrates for Pox. Prussian blue agar has been developed to detect oxidase activity in bacterial extracts (20). This system was adapted to be used with tryptic soy agar plates so that hydrogen peroxide production could be detected in STYM1 extracts. Halos of Prussian blue form around wells in the agar plate filled with hydrogen peroxide. The reaction is specific and the diameter of the halo is dependent on the concentration of hydrogen peroxide (FIG. 5A).

Figure 5B:
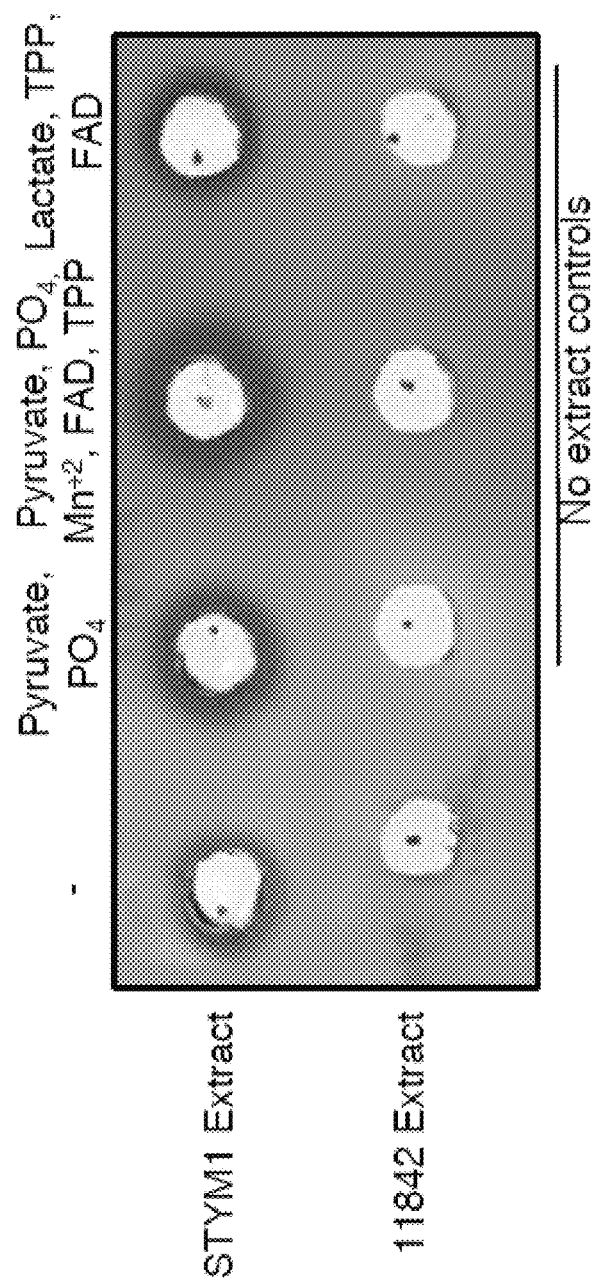
Figures 5C, 5D:
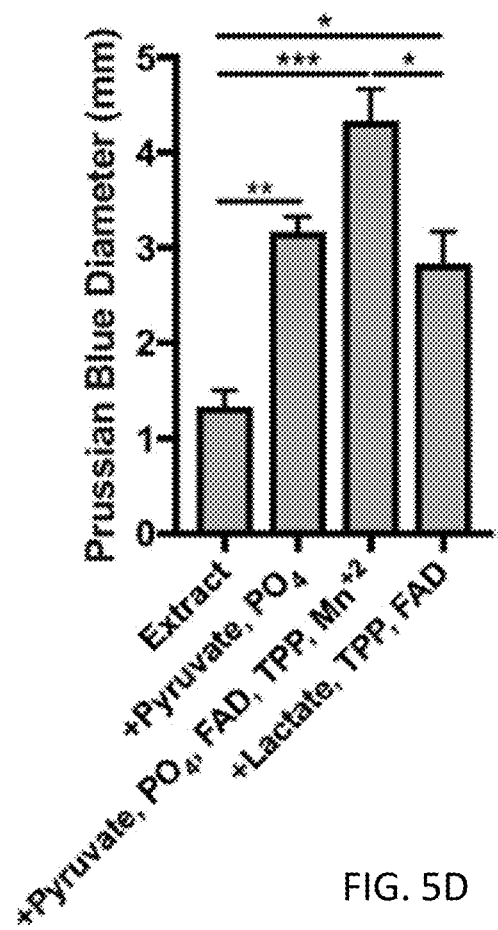
FIG. 5D shows measurements of the Prussian blue diameter minus the inner well (6-mm diameter) for the STYM1 extract samples in panel B from three independent experiments. Error bars represent standard errors of the mean. Statistical significance determined by one-way ANOVA corrected for multiple comparisons (*, $P<0.05$; , $P<0.01$; *, $P<0.001$).

The STYM1 extract alone produces a moderate amount of hydrogen peroxide on Prussian blue plates in the range of 500 μM to 1 mM while the 11842 strain extract produces no detectable hydrogen peroxide (FIG. 5B). However upon supplementation with 50 mM pyruvate and phosphate, the hydrogen peroxide production significantly increased as measured by the Prussian blue halo diameter. Hydrogen peroxide production was even further enhanced by the addition of the cofactors of the Pox enzyme: 10 mM $Mn^{+2}$, 15 μM FAD, and 300 μM TPP. Supplementation of the STYM1 lysate with Lox substrate and cofactors 150 mM DL-Lactate, 300 μM TPP, and 15 μM FAD resulted in a modest enhancement of hydrogen peroxide production, but not to the level observed with supplementation of Pox substrates and cofactors (FIG. 5B and FIG. 21). These data suggest that Pox is likely the main producer of hydrogen peroxide in STYM1 extracts.

Figure 11:
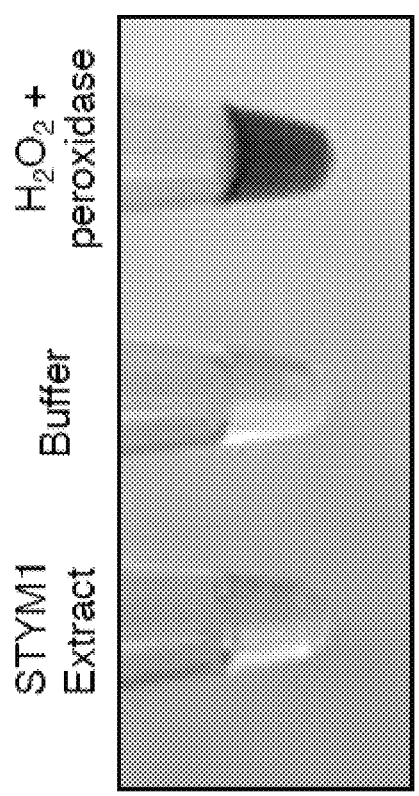
FIG. 11 demonstrates STYM1 extract does not have laccase activity toward syringalazine substrate. STYM1 extract was added to a mixture of horseradish peroxidase and syringalazine to assay for laccase activity. A buffer control was included that contained no STYM1 extract and a positive control containing hydrogen peroxide, peroxidase, and syringalazine was used to visualize oxidation of syringalazine.
Figure 12:
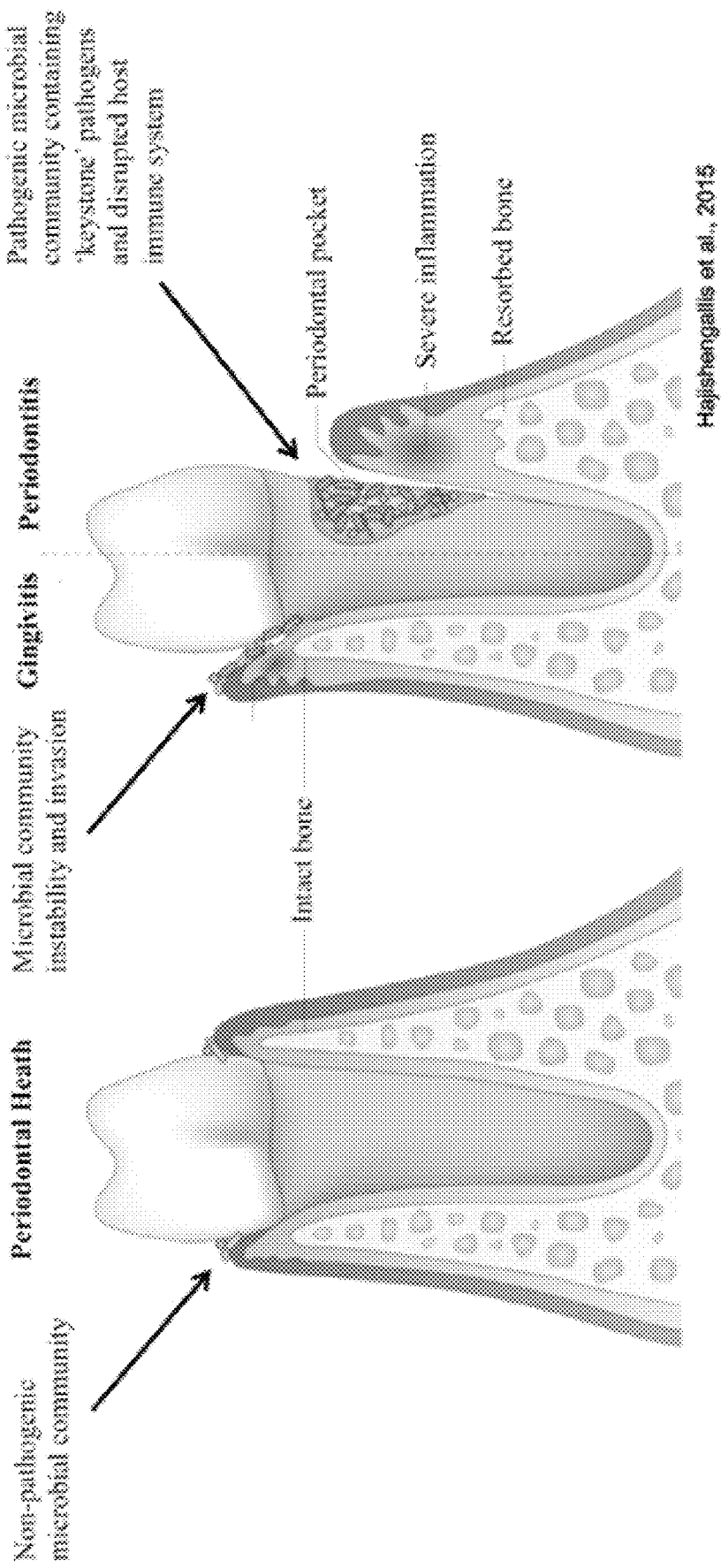
FIG. 12 demonstrates polymicrobial synergy and dysbiosis in periodontitis. The mechanism by which the inhibiting strain of *L. delbruecki* exerted its effect was through the enzymic activity of pyruvate oxidase. Understanding the mechanisms by which probiotic bacteria can inhibit growth of pathogenic strains may be important in the development of preventative strategies for periodontitis.
Figure 12:
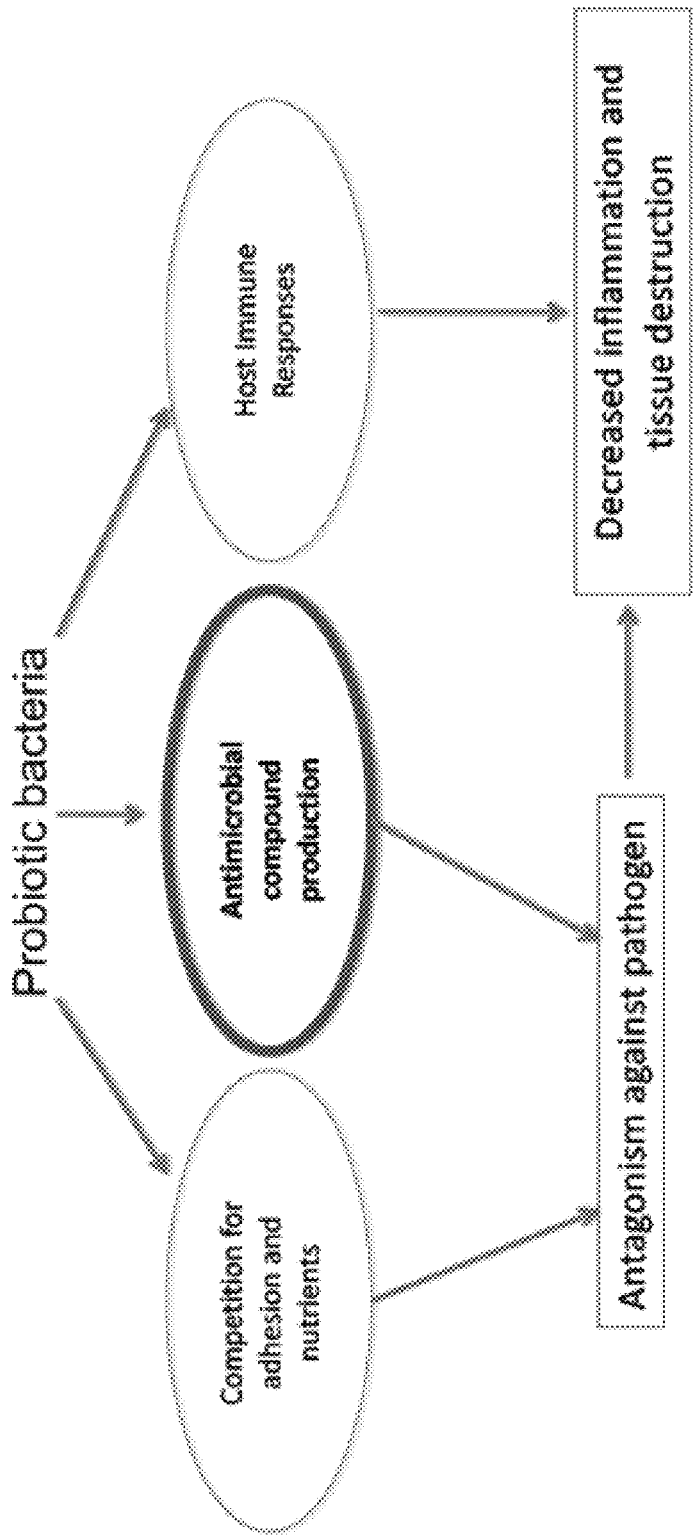

The substrate for the multicopper oxidase is unknown. Multicopper oxidases are a large family of proteins consisting of tyrosinases, monooxygenases, dioxygenases, and laccases among others (29). Most of these enzymes do not produce hydrogen peroxide. However, laccases have been characterized in some fungi and several have been identified in bacterial species, and bacterial laccases are able to produce hydrogen peroxide in some cases (30-32). Generally, the substrates of laccases are polyphenols and aromatic amines. To test whether laccase activity exists in STYM1 extracts, the extract's ability to oxidize the common laccase substrate, syringalazine was examined (33). STYM1 extract was unable to oxidize the syringalazine substrate suggesting that the multicopper oxidase is not a laccase or at least cannot use syringalazine as a substrate (FIG. 11).

Treatment of STYM1 Extracts with Oxidase Inhibitors

To further confirm the involvement of Pox in hydrogen peroxide production in STYM1 extracts, several inhibitors being described for Pox, Lox, and multicopper oxidases were used. Sodium sulfite is an inhibitor of flavin-dependent oxidases as the sulfite deactivates the flavin moiety by forming a covalent adduct to the molecule (34, 35). Both Pox and Lox are flavin-dependent oxidases, so both should be inhibited by sodium sulfite. As Pox coordinates a metal ion, it can be inhibited by treatment with EDTA. Oxalate acts as a specific inhibitor of Lox presumably by blocking the active site (36). Lastly, several multicopper oxidases are known to be inhibited by treatment with sodium azide, which disrupts the copper coordination in the protein (37).

Each of these inhibitors were tested for their ability to abolish the inhibitory activity seen in STYM1 extracts. Sodium azide treatment had no effect on the inhibitory activity even when tested over a wide range of concentrations suggesting that multicopper oxidase is not the inhibitory protein (FIG. 6A). Sodium oxalate treatment also had no effect on the STYM1 extract indicating that lactate oxidase may not be the primary hydrogen peroxide producing protein (FIG. 6B). However, treatment with sodium sulfite completely abrogated the inhibitory activity of STYM1 extract suggesting that Pox and/or Lox are responsible for hydrogen peroxide production (FIG. 6C). Furthermore, EDTA treatment fully blocked the ability of STYM1 extract to inhibit Pg and supplementation of $Mn^{+2}$ in excess of the EDTA concentration restored inhibitory activity in the extract (FIG. 6D). Taken together, these data suggest Pox is the primary hydrogen peroxide-producing enzyme in STYM1 extracts.

LDBND_1487 Pox is More Highly Expressed than LDBND_2051 Pox.

Figures 7A, 7B, 7C:
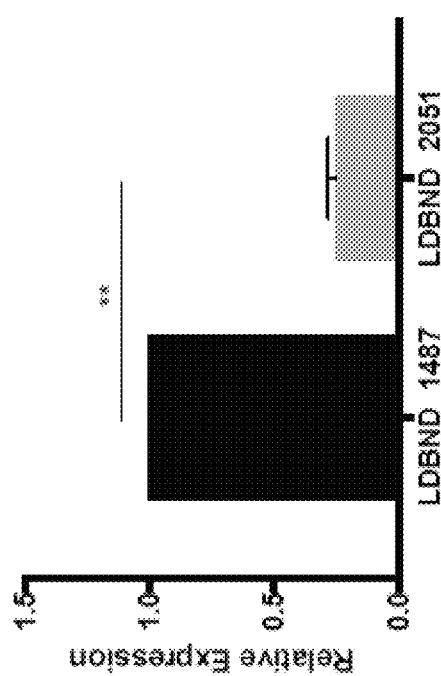
FIGS. 7A-7C demonstrate LDBND_1487 pox is more highly expressed than LDBND_2051 pox.

STYM1 encodes two predicted pox genes (LDBND_1487 and LDBND_2051) but only one (LDBND_1487) is unique to the STYM1 strain. Amino acid sequence alignment revealed that the protein sequences between the two genes are highly similar with only four amino acid substitutions and one insertion of six amino acids (FIG. 7A). Promoter analysis revealed the presence of the canonical −35 and −10 sequence upstream of LDBND_1487, but identified several mismatches with the canonical sequence upstream of LDBND_2051 (FIG. 7B). Therefore, it was decided to determine if the two genes differ in their expression. Indeed, it was found that LDBND_1487 was expressed at a significantly higher level than that of LDBND_2051 under the conditions tested (FIG. 7C). Expression was approx. 4-fold higher at the transcript level, but could you see any differences at the protein level?

Purified Pox is Catalytically Active and is Sufficient to Inhibit Pg Growth In Vitro.

Figure 8A:
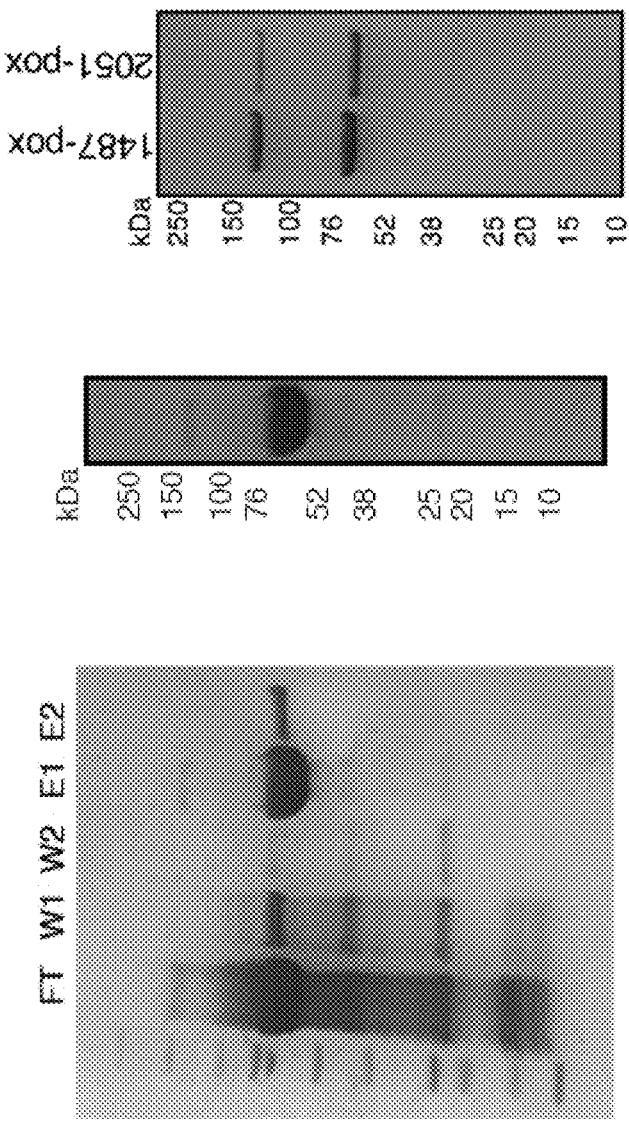
FIGS. 8A-8D demonstrate purified LDBND_1487 Pox is catalytically active and is sufficient to inhibit *P. gingivalis* in vitro.
Figure 8B:
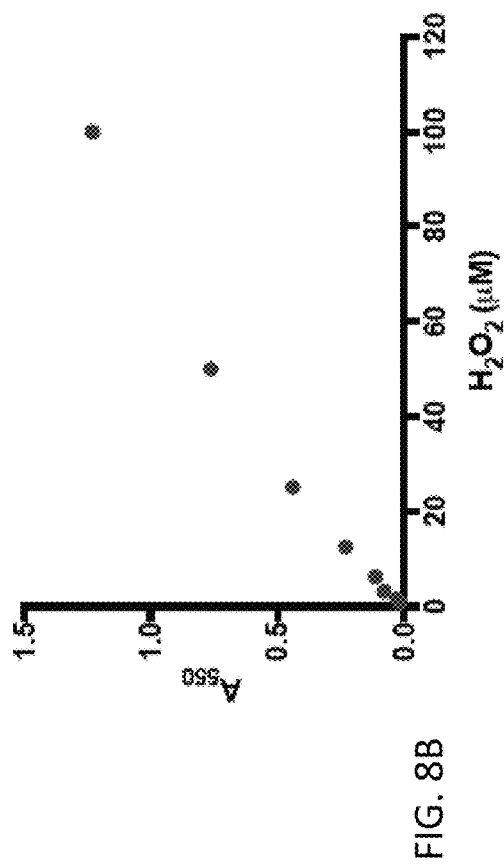
Figure 8D:
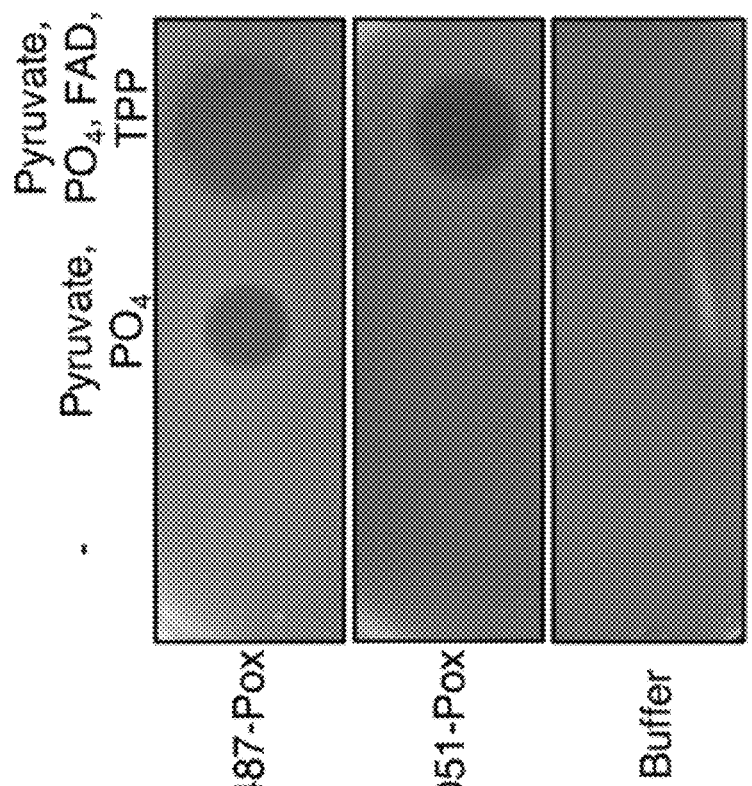
Figure 8C:
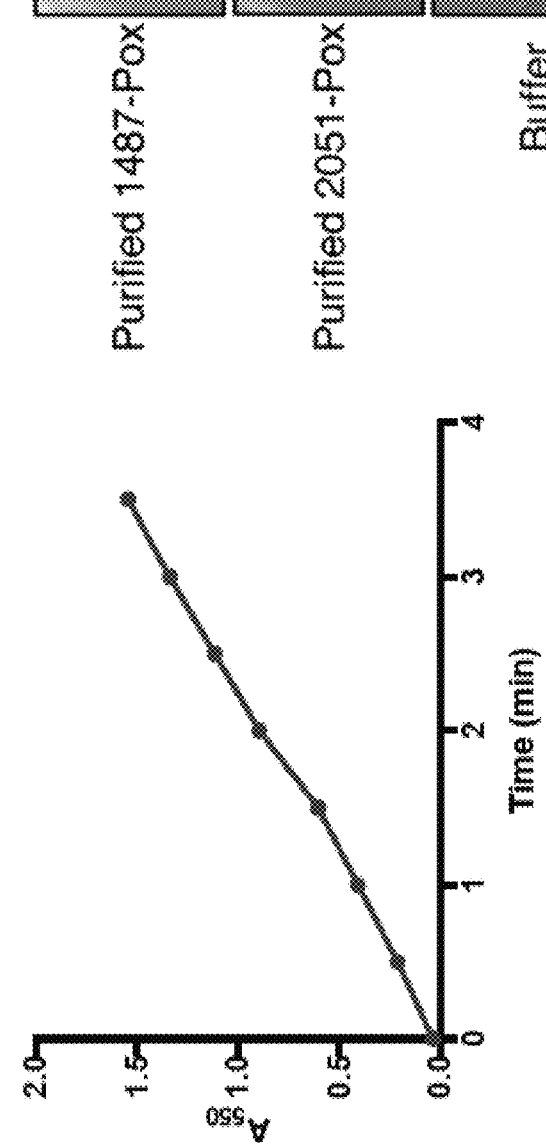
Figure 8E:
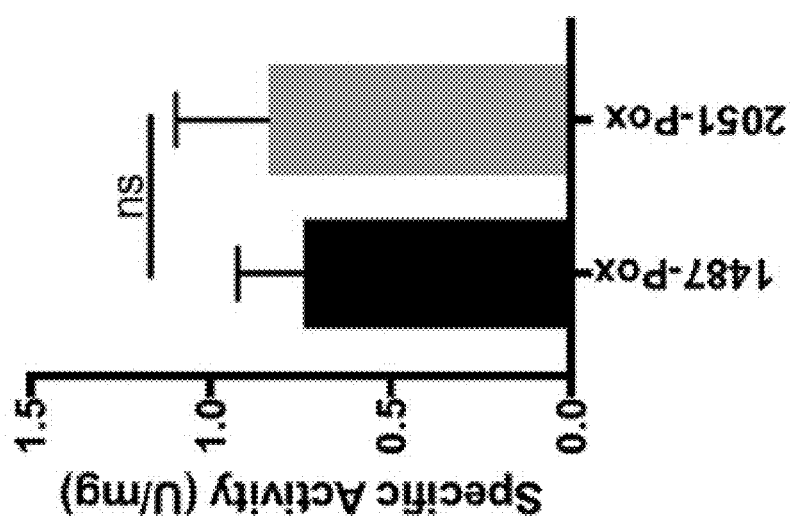
FIG. 8E shows pyruvate oxidase activity was measured by the oxidative coupling reaction, which utilizes the horseradish peroxidase-catalyzed formation of a quinoneimine dye with an absorbance at 550 nm. The assay measures $H_2O_2$ production by the Pox enzyme. Pyruvate oxidase activity was determined by measuring the change in $A_{550}$ per min and calculating the activity according to the equation in Materials and Methods. One unit of Pox activity is defined as the production of 1 μmol of $H_2O_2$ per min. The mean specific activity (U/mg) of 1487-Pox and 2051-Pox in at least three different purifications is shown. Error bars represent the standard errors of the mean, and significance was determined by a two-tailed t test (ns, not significant).

Taken together, the above data strongly suggest that LDBND_1487 Pox is the major, if not the sole, producer of hydrogen peroxide in STYM1 extracts. Thus, a his-tagged version of Pox was generated and the enzyme was purified on a Ni-NTA column (FIG. 8A). The eluted Pox fraction had a yellowish hue, which is characteristic of flavin-containing enzymes. An oxidative coupling reaction was used to assay for pyruvate oxidase activity. The reaction consisted of pyruvate, phosphate, purified pox enzyme, FAD, TPP, 4-aminoantipyrine, N-Ethyl-N-(2-hydroxy-3-sulfopropyl)-m-toluidine, and horseradish peroxidase that results in the formation of a quinoneimine dye upon hydrogen peroxide production via Pox that is measurable by an increase in absorbance at 550 nm. One unit of Pox activity is defined by the production of 1 μmol of $H_2O_2$ per minute. Extrapolating from the standard curve, it was determined that approximately 2.4 U/mL of Pox activity were present in the purified Pox sample (FIGS. 8B-8C).

The ability of purified recombinant Pox to inhibit Pg growth in an agar overlay assay was tested. Aliquots of Pox alone or Pox supplemented with either substrate or substrate and FAD and TPP were spotted onto an agar plate and then overlaid with a soft agar inoculated with Pg. Purified Pox alone was unable to inhibit Pg growth in the overlay. However, Pox supplemented with only pyruvate and phosphate produced a clear zone of inhibition in the agar overlay indicating Pox was purified with native FAD and TPP tightly bound. Furthermore, Pox supplemented with substrate and FAD and TPP produced an even larger zone of inhibition. The substrates and cofactors alone had no effect on Pg growth indicating that the inhibition is specific to the catalytic action of Pox (FIG. 8D). Together, these data demonstrate that Pox is sufficient to inhibit Pg growth in vitro.

Discussion

In this report, the mechanism of antagonism of a probiotic strain of *Lactobacillus delbrueckii* against the oral pathogen *Porphyromonas gingivalis* was described. The inhibitory capacity of Ld is strain specific underscoring the importance of strain selection not simply species selection in developing probiotic therapeutics. It was demonstrated that the STYM1 strain of Ld releases intracellular proteins via autolysis that are capable of producing inhibitory amounts of hydrogen peroxide. Strong evidence was presented via studies using oxidase inhibitors, supplementation with enzyme substrates/cofactors, and purification of recombinant protein that the main, if not sole, producer of hydrogen peroxide is the pyruvate oxidase (Pox, LDBND_1487).

*Lactobacillus* species are well known to produce a wide variety of antimicrobial proteins, collectively referred to as bacteriocins. These proteins range from small peptides to large proteins over 30 kDa with diverse mechanisms of action (38). There is substantial interest in developing these bacteriocins into novel antibiotics and preservatives in the food industry (39). One other mechanism by which *Lactobacillus* species can antagonize growth of other bacteria is through the production of hydrogen peroxide ($H_2O_2$). Hydrogen peroxide-mediated killing occurs through the production of superoxide and hydroxyl radicals via fenton chemistry with intracellular iron, which ultimately damages the DNA leading to cell death. Consistent with this, transposon mutants in the iron transporter feoB2 were recovered that are more resistant to killing by STYM1 and recombinant Pox. Hydrogen peroxide may also oxidize sulfhydryl groups in proteins and promote the peroxidation of unsaturated cytoplasmic membrane lipids (26).

Hydrogen peroxide can be generated in *lactobacillus* species by several different enzymes including pyruvate oxidase, lactate oxidase, NADH oxidase, and NADH flavin-dependent reductases (27, 40, 41). Several *lactobacillus* strains produce enough hydrogen peroxide to inhibit the growth of pathogens like *Listeria monocytogenes, Staphylococcus aereus*, and *Pseudomonas* species (42-44).

The STYM1 strain encodes two pyruvate oxidase genes: LDBND_1487 and LDBND_2051. Genome analysis of STYM1 relative to non-inhibitory strains revealed that LDBND_1487 is truncated in non-inhibitory strains but LDBND_2051 is intact. It is not uncommon for *lactobacillus* species to encode multiple pyruvate oxidase genes in their genomes. For example, *Lactobacillus plantarum* encodes five pyruvate oxidase genes of which only two are responsible for hydrogen peroxide production and Pox activity despite the other pox genes retaining amino acid residues important for catalysis and substrate and cofactor binding (45). This observation could be due to expression levels of the different pox genes. In the STYM1 strain, LDBND_1487 pox is expressed more highly than LDBND_2051 pox likely explaining how LDBND_1487 pox is the main component of Pox activity in our samples. The expression data on LDBND_1487 and LDBND_2051 in the STYM1 strain is also confirmed by promoter analysis of the two genes. LDBND_1487 has a −35 and −10 sites that are identical to the consensus sequence in *E. Coli* and in *lactobacillus* species (46-48). Alternatively, the LDBND_2051 pox promoter has several mismatches in the −35 and −10 sites in bases that have been shown to be critical for promoter binding by sigma factors.

Interestingly, the regulation of LDBND_1487 pox in the STYM1 strain appears to be different than in some other organisms. In other organisms pox is highly expressed in stationary phase and under glucose limitation, but is repressed in anaerobic conditions (27). This regulatory pattern of pox is consistent with the results in that Pox was detected by mass spectrometry in extracts from stationary phase STYM1 Ld grown in BHI, which is considered to be a low glucose condition (0.2%) for *lactobacillus* species. However, these cells were grown under anaerobic conditions, which is a condition where pox is expected to be repressed. It is possible that the positive regulation of pox by growth phase and glucose limitation overrides the repression under anaerobic conditions.

It has also been shown that of two pox genes that are highly expressed in *L. planatrum*, one is strongly repressed in stationary phase while the other's expression is maintained (45). In addition, the repression of Pox under anaerobic conditions results in about a 50% decrease in expression levels in *E. coli*, but at a level that is still detectable suggesting that while there is repression of Pox under anaerobic conditions there is likely still some level of Pox produced (49). It has been confirmed that LDBND_1487 is expressed and translated under the conditions of the assay based on the qRT-PCR and mass spectrometry data indicating this may be a novel regulatory pattern of pox under anaerobic conditions. Another explanation of the presence of two pox genes but the major activity of one is that one Pox enzyme may have different substrate specificity. It has been demonstrated that *L. plantarum* Pox can use the alternative substrates methylglyoxal and acetaldehyde supporting this possibility (28).

The Pox enzyme has been characterized in other organisms. In *Lactobacillus plantarum*, Pox is involved in acetate production during stationary phase where it converts pyruvate to acetylphosphate, which is converted to acetate by acetate kinase with the production of ATP (27, 45). This production of ATP is considered to be a major reason for the increased biomass during aerobic growth of *L. plantarum* (27). In *Streptococcus pneumoniae*, Pox accounts for the majority of hydrogen peroxide production and similarly to *L. plantarum* is involved in acetate and ATP production in concert with lactate oxidase, lactate dehydrogenase, and acetate kinase (50). In some Ld strains, it is known that hydrogen peroxide can be produced by NADH oxidase, but STYM1 does not encode a predicted NADH oxidase (40). In *Lactobacillus johnsonii*, an NADH flavin reductase was found to be the major producer of hydrogen peroxide (41). Interestingly, STYM1 does encode homologues of the NADH flavin reductase (LDBND_1905 and 1906), but these genes are also present in the non-inhibitory strains. Together, these observations suggest that different species can have distinct enzymes that are the main producers of hydrogen peroxide.

It remains an interesting question as to the role of hydrogen peroxide producing enzymes in lactic acid bacteria considering they do not encode catalases and many do not encode NADH peroxidases or alkyl hydroperoxide reductases, including the STYM1 strain. Several species including Ld produce self-inhibitory levels of hydrogen peroxide upon aeration, which presumably would be a fitness disadvantage. However, hydrogen-peroxide-producing lactobacilli have been associated with the maintenance of healthy gut and vaginal microbial communities and immune function. There is strong evidence that women with higher levels of hydrogen peroxide-producing lactobacilli have a decreased risk for developing bacterial vaginosis (51, 52). Retaining hydrogen peroxide producing enzymes may help these bacteria maintain their specific niche and outcompete other organisms in the community or invading pathogens. One study found that PPAR-γ, which is involved in anti-inflammatory responses and immune homeostasis, is activated by hydrogen peroxide produced by *Lactobacillus crispatus* (53). This aspect of hydrogen peroxide-producing bacteria is particularly attractive in the context of periodontitis as much of the pathophysiology is driven by an overactive immune response.

These characteristics, and that Ld has the generally regarded as safe (GRAS) designation, make the STYM1 strain of Ld a strong candidate for use as a probiotic strain in the treatment and/or prevention of periodontitis. However, the adhesion and colonization properties of Ld in the oral cavity could be problematic. The oral cavity is not the natural niche of Ld although there are other *Lactobacillus* species that are permanent colonizers. It is likely that the Ld strain is a transient colonizer of the oral cavity, yet with daily consumption of a yogurt containing Ld it may be possible to have stable colonization. It may be useful to engineer an Ld strain that is better able to colonize and adhere to the tooth surface or introduce the STYM1 pox gene into a heterologous strain or species to overcome this issue. In addition, it was also shown that Pg resistant mutants to STYM1 extracts are deficient in the feoB2 iron transporter which has been shown to be an essential gene in vivo in Pg strain W50 (23). This makes the development of resistance to STYM1-mediated killing in vivo very unlikely furthering the attractiveness of STYM1 for probiotic use.

Hydrogen peroxide production in the oral cavity is well known to occur primarily by resident streptococcal species. This hydrogen peroxide production is thought to play an important role in shaping the oral microbial community and in fact there is a strong correlation between hydrogen peroxide production and the presence of pyruvate oxidase genes in the oral microbiome (54, 55). *Streptococcus sanguinis* is considered to be one of the major producers of hydrogen peroxide in the oral cavity (56). Its hydrogen peroxide production has been shown to be almost exclusively through the activity of pyruvate oxidase and not other oxidases like lactate oxidase which are present in the genome (57). Interestingly, the abundance of the sanguis group of *streptococcus* was negatively correlated with the number of periodontal pathogens present in the oral microbial community indicating that pyruvate oxidase-derived hydrogen peroxide can have a substantial impact on the community constituents particularly anaerobic periodontal pathogens (58).

Beyond the utility of hydrogen peroxide production by oxidases, particularly Pox, in probiotic action, Pox enzymes have industrial and practical applications. Pox enzymes are currently used to measure pyruvate and phosphate concentrations in some clinical and non-clinical samples and there is interest in developing biosensors with Pox enzymes (59-61). One limitation to the effectiveness of other Pox enzymes is the requirement for supplementation with the cofactors TPP and FAD increasing the cost and decreasing the longevity of the enzyme. The recombinant STYM1 Pox enzyme was purified with associated cofactors tightly bound as the enzyme was active without the addition of exogenous cofactors. This is in contrast to some other Pox enzymes and represents an attractive quality of the enzyme for practical and industrial applications (61).

Many of the mechanisms of probiotic function remain poorly understood hindering the rational design of probiotic strains of bacteria. In this report, the molecular mechanism by which a potential probiotic strain of *L. delbrueckii*, STYM1, inhibits the periodontal pathogen *P. gingivalis* is presented. The major hydrogen peroxide-producing enzyme pyruvate oxidase was purified and it was shown to have unique characteristics relative to other Pox enzymes. The STYM1 strain could be developed into a useful probiotic strain for the treatment and/or prevention of periodontal disease and inform the design of other probiotic strains of bacteria.

Materials and Methods

Bacterial Strains, Media, and Growth Conditions

Bacterial strains, plasmids, and primers used in the study are listed in FIG. 20 and FIG. 21. *P. gingivalis* strain W83 was grown on blood agar plates containing tryptic soy agar supplemented with defibrinated sheep's blood (5% vol/vol), yeast extract (2 mg/mL), hemin (5 µg/mL), and menadione (0.5 µg/mL). Broth cultures of *P. gingivalis* were grown in brain-heart infusion broth supplemented with yeast extract (1 mg/ml), hemin (5 µg/ml), and menadione (0.5 µg/ml), sodium bicarbonate (1 µs/ml), sodium thioglycolate (0.25 µg/ml), and cysteine (0.5 µg/ml). For agar overlay assays, tryptic soy agar plates supplemented with yeast extract (2 mg/mL), hemin (5 µg/ml), and menadione (0.5 µg/ml), sodium bicarbonate (1 µg/ml), sodium thioglycolate (0.25 µg/ml), and cysteine (0.5 µg/ml) were used. Gentamicin (25 µg/mL), erythromycin (5 µg/mL), and tetracycline (1 µg/mL) were used when appropriate for *P. gingivalis* growth and mutant selections. All *P. gingivalis* strains were grown at 37° C. in GasPak™ EZ Anaerobe Pouch Systems (BD Biosciences) for 48 hrs for broth cultures and 4-6 days for plate-based assays. *L. delbrueckii* strains were grown in MRS (BD biosciences) broth or agar or in BHI broth described above. All *L. delbrueckii* were grown at 37° C. GasPak™ EZ Anaerobe Pouch Systems (BD Biosciences). *Escherichia coli* DH5α, S17-1 λpir, and LOBSTR (LOBSTR BIO BASIC Inc; a gift from Katya Heldwein) were used for cloning, conjugation, and protein purification, respectively. Ampicillin (100 µg/mL) was used when appropriate in LB agar or broth.

*L. delbrueckii* Extracts and Supernatants

*L. delbrueckii* colonies were inoculated into BHI (10 mL) and grown anaerobically overnight at 37° C. For supernatants, the overnight culture was harvested by centrifugation for 10 minutes a 3,200×g at room temperature. The supernatant was aspirated and passed through a 0.22 µm filter to obtain cell-free supernatant. For cell extracts, four 10 mL cultures were combined and harvested by centrifugation for 10 minutes at 3,200×g at room temperature. The cell pellet was washed once with 1 mL 20 mM Bis-Tris pH 7.0 and then centrifuged at 9,300×g for 5 minutes. The cell pellet was resuspended in 1 mL 20 mM Bis-Tris pH 7.0 with 1× cOmplete EDTA-free protease inhibitor cocktail mix (Roche). The cell suspension was sonicated on ice with three rounds of 15×1 second bursts. To remove cell debris, the suspension was centrifuged at 16,000×g at 4° C. for 15 minutes. The supernatant was aspirated and filtered through a 0.22 filter yielding the soluble cell extract which was used in subsequent agar overlay assays and Prussian blue assays. Total protein concentration was determined by BCA assay (Pierce).

For large scale extraction for use in fractionation experiments, an overnight culture of L. delbrueckii grown in BHI was diluted 1:50 into 600 mL of BHI and incubated overnight at 37° C. The same steps were performed as above except the buffer volumes were 40 mL.

Agar Overlay Assay and Spot Assay

For agar overlays with live L. delbrueckii cultures, 2-5 µL of culture was spotted onto a BHI agar glass plate and allowed to dry. The plate was incubated anaerobically for 48 hrs at which point the L. delbrueckii cells were killed by exposure to chloroform vapor for 3 hr, allowed to de-gas for 30 minutes, then overlaid with 4 mL of soft BHI agar (0.7%) inoculated with the W83 strain of P. gingivalis to an OD600 of approximately 0.1. The plates were incubated anaerobically for 2-3 days at 37° C. and zones of inhibition were analyzed and plates were imaged. For agar overlays with L. delbrueckii extracts, 10-30 µL of extract was spotted onto TSA 120 or BHI plates and allowed to dry. These plates were overlaid, incubated, and imaged as described above.

In the spot assays, 5 µL of L. delbrueckii culture was spotted onto a BHI plate, allowed to dry, and incubated for 48 hrs anaerobically at 37° C. 5 µL of P. gingivalis culture was then spotted directly adjacent to the spot of L. delbrueckii growth, allowed to dry, and incubated anaerobically for 48 hr at 37° C. Plates were analyzed for zones of inhibition and imaged.

Growth Curves

L. delbrueckii was inoculated into 1 mL of BHI (which contains 0.2% glucose) or BHI supplemented with 2% glucose at an OD600 of 0.02. Growth was monitored using a Biotek HT spectrophotometer. OD600 was measured hourly over a 48 hr period.

Biochemical Characterization of STYM1 Extract

Prior to testing in an agar overlay assay, STYM1 extracts were treated with either heat, proteinase K, or passage through a 10 kDa MWCO filter (Millipore). In addition, the STYM1 extract was eat-inactivated at 95° C. for 20 minutes. For proteinase K treatment, 2 µL of proteinase K (20 mg/mL) (Qiagen) was added to 18 µL of extract and incubated for 1 hr at 37° C. Buffer was also added to a separate sample of extract and incubated for 1 hr at 37° C. as well. For heat-inactivated proteinase K, proteinase K was heated at 95° C. for 20 minutes prior to addition to STYM1 extract. For 10 kDa MWCO treatment, the STYM1 extract was flowed through a 10 kDa MWCO filter (Millipore) according to the manufacturer's instructions. The concentrate and the flow-through were tested in an agar overlay assay.

STYM1 extracts were also treated with catalase and known oxidase inhibitors prior to testing in agar overlay assays. For catalase treatment, 10 µg of bovine liver catalase (Sigma) was added to STYM1 extracts before the agar overlay assay. To separate aliquots of STYM1 extract, Sodium oxalate (Sigma) was added to final concentrations of 6.6 mM and 66 mM, sodium sulfite (Sigma) to a final concentration of 20 mM, and sodium azide (Fischer) was added to final concentrations of 1 mM, 100 µM, and 10 µM. For EDTA treatment, EDTA was added to a final concentration of 5 mM and incubated for 1 hr at room temperature prior to agar overlay or manganese supplementation. In some EDTA treated samples, $MnCl_2$ was added to final concentrations of 5 mM and 10 mM after the 1 hr incubation with EDTA and samples were incubated for an additional hour at room temperature before plating on the agar overlay assay.

Fractionation of STYM1 Extracts

Proteins from 40 mL cell extracts of STYM1 cultures were precipitated by step-wise ammonium sulfate precipitation. Briefly, ammonium sulfate was added to give 30, 40, 50, and 60% saturation during each step. After addition of each step, the extract was rotated at 4° C. for 1 hr then centrifuged at 10,000×g for 20 minutes at 4° C. The supernatant was used for the next step-up of saturation, while the protein pellet was washed once in 40 mL of the same saturation of ammonium sulfate buffer then solubilized in 1-2 mL of 20 mM Bis-Tris pH 7.0 with cOmplete EDTA protease inhibitor cocktail. The solubilized pellet from each step was then tested in an agar overlay assay for inhibitory activity toward Pg.

Ammonium sulfate precipitation fractions with inhibitory activity were dialyzed overnight against 500 volumes of 20 mM Bis-Tris pH 7.0 in 6-8 kDa MWCO dialysis tubing. Anion exchange chromatography of these samples was carried out on duo-flow system (Biorad) with a Hi-Trap Capto Q 1 mL column (GE Healthcare). The column was equilibrated with 5 mL of 20 mM Bis-Tris pH 7.0 after which the sample was applied to the column and bound protein was eluted with a linear gradient of 0 to 1M NaCl in 20 mM Bis-Tris pH 7.0 over 25 mL at 1 mL/min flow rate. Each 1 mL fraction was tested for inhibitory activity in an agar overlay assay. Fractions with inhibitory activity were pooled and concentrated to 500 µL on 10 kDa MWCO spin column (Millipore) prior to fractionation by size exclusion chromatography using a Superdex 200 column in 20 mM Bis-Tris pH 7.0. Each 1 mL fraction was tested for inhibitory activity in an agar overlay assay. Protein content of each fraction was assessed by SDS-polyacrylamide gel electrophoresis (PAGE) and Coomassie staining. Protein bands of interest were excised from the gel and analyzed by tandem liquid chromatography mass spectrometry (LC-MS/MS). LC-MS/MS analysis was performed by the Taplin Biological Mass Spectrometry Facility at Harvard Medical School according to their standard protocol.

Transposon Library Screen and STYM1 Extract Exposure Assays

An aliquot of the P. gingivalis W83 transposon library was adjusted to an $OD_{600}$ of 1.4 in 20 mM Bis-Tris pH 7.0. For exposure experiments with W83 or individual transposon mutants, the strains were grown for 48 hr in BHI at which point they were harvested by centrifugation at 9,300×g for 5 minutes and then resuspended in 20 mM Bis-Tris pH 7.0 at an OD600 of 1.4. To 500 µL of these suspension, STYM1 crude extract was added to a final concentration of 1 mg/mL of total protein. The suspension was incubated for 3 hr at 37° C. Serial dilutions were plated on blood agar plates and incubated at 37° C. for 6 days to enumerate colony forming units. Surviving colonies of transposon mutants were re-isolated on blood agar plates and their genomic DNA prepared with the DNeasy Blood and Tissue kit (Qiagen).

Semi-Random PCR

The transposon:genome junction of isolated transposon mutants was determined by semi-random PCR which consists of two rounds of PCR. The first round used primers pWH2_seq1 and arb1 and consisted of initial denaturation at 96° C. for 3 minutes followed by 5 cycles of 96° C. for 1 minute, annealing at 30° C. for 1 minute, and extension at 72° C. for 1 minute followed by an additional 35 cycles but with the annealing step at 55° C. and a 5 minute extension at 72° C. The second round used 2 µL of the first reaction as template and used primer pWH2_seq2 and arb2. The reaction consisted of initial denaturation at 96° C. for 3 minutes followed by 35 cycles of 96° C. for 1 minute, annealing at 55° C. for 1 minute, and extension at 72° C. for 1 minute followed by a final extension at 72° C. for 5 minutes. Samples were purified using the Promega Wizard kit according to manufacturer instructions. Samples were sequenced with the pWH2_seq3 primer and the sequence was aligned to the W83 genome to determine the location of transposon insertion.

Construction of feoB2 Transposon Mutant Complement

The wild type feoB2 gene (PG1294) and its native promoter (200 bp upstream) were PCR amplified, ligated into pT-COW (18), and transformed into TOP10 E. coli (Thermo). Clones were confirmed by restriction digest, PCR, and sequencing. The new plasmid, pT-COW_FeoB2, was transformed into S17-1 λpir E. Coli (19). The S17-1 λpir E. coli harboring the pT-COW_FeoB2 plasmid was conjugated with the Tn-feoB2 strain by combining 750 µL of mid-logarithmic phase cultures ($OD_{600}$ 0.4-0.8) of each strain and centrifuging at 9,600×g for 2 min. The cell pellet was resuspended in 375 µL of sterile PBS, transferred to a blood agar plate with no antibiotics, and incubated aerobically at 37° C. for 5 hours. The growth on the plate was scraped into 300 µL of PBS then plated on blood agar plates containing gentamicin and tetracycline and incubated anaerobically at 37° C. for 7 days. Complementation was confirmed by PCR and sequencing.

Prussian Blue Hydrogen Peroxide Detection

Prussian Blue TSA plates were made as described previously (20). To assay for hydrogen peroxide production, 6 mm wells were cut into the agar and 50 µL of either different concentrations of hydrogen peroxide or test samples were added and incubated for 30 minutes to 2 hours at room temperature prior to imaging and measuring the diameter of the Prussian Blue halo. STYM1 extracts were supplemented with oxidase substrates and cofactors as follows. For pyruvate oxidase, the substrates sodium pyruvate (Sigma) and sodium phosphate (Fisher) were added to a final concentration of 50 mM each and the cofactors thiamine pyrophosphate (TPP) (Sigma), flavin adenine dinucleotide (FAD) (Sigma), and $MnCl_2$ were added to final concentrations of 300 µM, 15 µM, and 10 mM, respectively. For lactate oxidase, DL-Sodium lactate was added to a final concentration of 150 mM to ensure there was 50 mM L-lactate available and the cofactors TPP and FAD were added to final concentrations of 300 µM and 15 µM, respectively.

Laccase Assay

STYM1 extract was added to a buffer solution containing 10 µM $CuSO_4$ and 100 µM syringalazine laccase substrate (Sigma). A buffer control and a positive control containing 5 mM hydrogen peroxide, 1 mg/mL horseradish peroxidase, and 100 µM syringalazine were also included in the assay.

RNA Isolation and qRT-PCR

Total RNA from L. delbrueckii STYM1 was isolated after overnight growth in BHI medium. 1 mL of the culture was centrifuged at 9,300×g for 10 minutes and resuspended in Trizol reagent (Ambion). RNA was isolated following the manufacturer's instructions. Total RNA was examined for integrity by gel electrophoresis. The RNA was treated with DNase using the turbo DNA-free kit according to the manufacturer instructions (Ambion). cDNA was generated using the ImProm-II reverse transcription system according to the manufacturer instructions (Promega).

qRT-PCR was performed with the iTaq Universal SYBR Green Supermix (Bio-Rad) on the CFX Connect Real-time PCR Detection System (Bio-Rad). Primer pairs amplifying a 150 bp product from cDNA of LDBND_1487 pox and LDBND_2051 pox were added to a final concentration of 400 nM. The primer pairs were designed at the regions of the two genes that displayed substantial sequence variation between each other where one primer had at least 6 mismatches relative to the same location in the other pox gene. Thermal cycling consisted of initial denaturation of 95° C. for 3 minutes followed by 39 cycles of 95° C. for 10 seconds and 60° C. for 30 seconds. Melt curves for the products were examined to ensure that a single amplicon was produced. Samples were run in triplicate and reverse-transcriptase controls were included to confirm the absence of genomic DNA. A standard curve for each primer pair was generated using STYM1 genomic DNA. Expression was normalized to the 16S ribosomal RNA gene.

Purification of Pyruvate Oxidase

LDBND_1487 pyruvate oxidase was PCR amplified from STYM1 genomic DNA using the primers listed in FIG. 21. The C-terminal primer encoded a glycine-serine linker followed by a 6-histidine tag and a stop codon. The PCR product was ligated into the pFLAG-CTC vector (Sigma) using the NdeI and XhoI restriction sites and transformed into DH5α E. coli resulting in the plasmid pFLAG-CTC_Pox. The construct was confirmed by PCR and sequencing. pFLAG-CTC_Pox was transformed into LOBSTR E. coli in which Pox was expressed as a C-terminal $His_6$-Pox. A 6 mL starter culture was incubate at 37° C. overnight in LB supplemented with 100 µg/mL of ampicillin. The starter culture was diluted 1:100 into 40 mL of LB supplemented with 100 µg/mL of ampicillin and grown at 37° C. until the $OD_{600}$ reached 0.4-0.8. The temperature was then shifted to 26° C. and the cells were incubated with 1 mM isopropyl-β-D-thiogalactopyranoside (IPTG) for 20 hours. The cells were harvested by centrifugation at 3,200×g for 10 minutes, resuspended in 1 mL PBS EDTA-free cOmplete protease inhibitor cocktail (Roche), and lysed by sonication on ice, as described above. The soluble cell lysate was harvested by centrifugation at 16,000×g for 15 minutes at 4° C. and filtered through a 0.22 µm filter to obtain cell-free soluble cell lysate. The soluble cell lysate was applied to a 1 mL bed volume of HisPure Ni-NTA resin (Thermo) and the eluate was applied a second time to the column to maximize protein binding. The column was washed twice with PBS containing 25 mM imidazole then bound protein was eluted from the column in PBS containing 250 mM imidazole. Protein purity was assessed by SDS-PAGE and Coomassie staining.

Pyruvate Oxidase Activity Assay

Pyruvate oxidase activity of recombinant Pox was assessed by an oxidative coupling reaction. The reaction consisted of 50 mM sodium pyruvate, 50 mM sodium phosphate, 15 µM FAD, 300 µM TPP, 0.03% N-Ethyl-N-(2-hydroxy-3-sulfopropyl)-m-toluidine (EHSTP) (Sigma), 0.015% 4-aminoantipyrine (Sigma), and 33 µg/mL horseradish peroxidase (Sigma). Typically a 1:10 dilution of purified Pox enzyme was then added in a total reaction volume of 1 mL. Immediately upon addition of purified Pox, the formation of a quinoneimine dye was measured by an increase in the absorbance at 550 nm which was recorded every 30 seconds at room temperature. Pox activity generates hydrogen peroxide, which is then used by peroxidase to oxidize EHSTP and 4-aminoantipyrine forming the quinoneimine dye. Pox activity is assessed by determining the change in absorbance at 550 nm per minute. 1 unit of Pox activity is defined as the production of 1 µmol of hydrogen peroxide per minute. A standard curve with known concentrations of hydrogen peroxide was used to determine the amount of quinoneimine dye formed under each condition. Activity was determined according to the following equation: specific activity=$[(\Delta A_{550}/\text{min})(\text{dilution factor})(\text{total reaction volume})]/[(36.88)(0.5)(\text{path length})(\text{sample volume})(C)]$, where the total reaction volume is 1 ml, the millimolar extinction coefficient of quinoneimine dye is 36.88, the factor of 0.5 was determined based on the fact that 1 mol of hydrogen peroxide produces 0.5 mol of quinoneimine dye, the light path length is 1 cm, the sample volume is 0.1 ml, and C is the concentration of undiluted enzyme in mg/ml.

REFERENCES

1. Hajishengallis G, Lamont R J. 2012. Beyond the red complex and into more complexity: the polymicrobial synergy and dysbiosis (PSD) model of periodontal disease etiology. Mol Oral Microbiol 27:409-419.
2. Schrezenmeir J, de Vrese M. 2001. Probiotics, prebiotics, and synbiotics—approaching a definition. Am J Clin Nutr 73:361S-364S.
3. Moayyedi P, Ford A C, Talley N J, Cremonini F, Foxx-Orenstein A E, Brandt L J, Quigley E M M. 2010. The efficacy of probiotics in the treatment of irritable bowel syndrome: a systematic review. Gut 59:325-332.
4. Delzenne N M, Neyrinck A M, Backhed F, Cani P D. 2011. Targeting gut microbiota in obesity: effects of prebiotics and probiotics. Nat Rev Endocrinol 7:639-646.
5. Yoo S-R, Kim Y-J, Park D-Y, Jung U-J, Jeon S-M, Ahn Y-T, Huh C-S, McGregor R, Choi M S. 2013. Probiotics L. plantarum and L. curvatus in combination alter hepatic lipid metabolism and suppress diet-induced obesity. Obes Silver Spring Md. 21:2571-2578.
6. de Sousa Moraes L F, Grzeskowiak L M, de Sales Teixeira T F, Gouveia Peluzio M do C. 2014. Intestinal microbiota and probiotics in celiac disease. Clin Microbiol Rev 27:482-489.
7. Bermudez-Humaran L G, Aubry C, Motta J-P, Deraison C, S 714 teidler L, Vergnolle N, Chatel J-M, Langella P. 2013. Engineering lactococci and lactobacilli for human health. Curr Opin Microbiol 16:278-283.
8. Nishiyama K, Seto Y, Yoshioka K, Kakuda T. Takai S, Yamamoto Y, Mukai T. 2014. Lactobacillus gasseri SBT2055 reduces infection by and colonization of Campylobacter jejuni. PloS One 9:e108827.
9. Carreras N L, Martorell P, Chenoll E, Genoves S, Ramon D, Aleixandre A. 2018. Anti-obesity properties of the strain Bifidobacterium animalis subsp. lactis CECT 8145 in Zucker fatty rats. Benef Microbes 9:629-641.
10. Panigrahi P, Panda S, Nanda N C, Satpathy R, Pradhan L, Chandel D S, Baccaglini L, Mohapatra A, Mohapatra S S, Misra P R, Chaudhry R, Chen H H, Johnson J A, Morris J G, Paneth N, Gewolb I H. 2017. A randomized synbiotic trial to prevent sepsis among infants in rural India. Nature 548:407-412.
11. Pandey K R, Naik S R, Vakil B V. 2015. Probiotics, prebiotics and synbiotics—a review. J Food Sci Technol 52:7577-7587.
12. Lin T-H, Lin C-H, Pan T-M. 2018. The implication of probiotics in the prevention of dental caries. Appl Microbiol Biotechnol 102:577-586.
13. Gruner D, Paris S, Schwendicke F. 2016. Probiotics for managing caries and periodontitis: Systematic review and meta-analysis. J Dent 48:16-25.
14. Ahola A J, Yli-Knuuttila H, Suomalainen T, Poussa T, Ahlstrom A, Meurman J H, Korpela R. 2002. Short-term consumption of probiotic-containing cheese and its effect on dental caries risk factors. Arch Oral Biol 47:799-804.
15. Krasse P, Carlsson B, Dahl C, Paulsson A, Nilsson A, Sinkiewicz G. 2006. Decreased gum bleeding and reduced gingivitis by the probiotic Lactobacillus reuteri. Swed Dent J 30:55-60.
16. Twetman S, Keller M K. 2012. Probiotics for caries prevention and control. Adv Dent Res 24:98-102.
17. Kim H-S, Kim Y-Y, Oh J-K, Bae K-H. 2017. Is yogurt intake associated with periodontitis due to calcium? PLOS ONE 12:e0187258.
18. GARDNER R G, RUSSELL J B, WILSON D B, WANG G-R, SHOEMAKER N B. 1996. Use of a Modified Bacteroides-Prevotella Shuttle Vector To Transfer a Reconstructed $^{N}{}_{L}$-1,4-D-Endoglucanase Gene into Bacteroides uniformis and Prevotella ruminicola B14. APPL Env MICROBIOL 62:7.
19. Simon R, Priefer U, Puhler A. 1983. A Broad Host Range Mobilization System for In Vivo Genetic Engineering: Transposon Mutagenesis in Gram Negative Bacteria. Nat Biotechnol 1:784-791.
20. Yu Z, Zhou N, Zhao C, Qiu J. 2013. In-Gel Determination of L-Amino Acid Oxidase Activity Based on the Visualization of Prussian Blue-Forming Reaction. PLOS ONE 8:e55548.
21. Pang X-Y, Cui W-M, Liu L, Zhang S-W, Lv J-P. 2014. Gene Knockout and Overexpression Analysis Revealed the Role of N-Acetylmuramidase in Autolysis of Lactobacillus delbrueckii subsp. bulgaricus Ljj-6. PLOS ONE 9:e104829.
22. Lortal S, Chapot-Chartier M-P. 2005. Role, mechanisms and control of lactic acid bacteria lysis in cheese. Int Dairy J 15:857-871.
23. Dashper S G, Butler C A, Lissel J P, Paolini R A, Hoffmann B, Veith P D, O'Brien-Simpson N M, Snelgrove S L, Tsiros J T, Reynolds E C. 2005. A Novel Porphyromonas gingivalis FeoB Plays a Role in Manganese Accumulation. J Biol Chem 280:28095-28102.
24. He J. Miyazaki H, Anaya C, Yu F, Yeudall W A, Lewis J P. 2006. Role of Porphyromonas gingivalis FeoB2 in Metal Uptake and Oxidative Stress Protection. Infect Immun 74:4214-4223.
25. Anaya-Bergman C, He J, Jones K, Miyazaki H, Yeudall A, Lewis J P. 2010. Porphyromonas gingivalis Ferrous Iron Transporter FeoB1 Influences Sensitivity to Oxidative Stress. Infect Immun 78:688-696.
26. Imlay J A. 2013. The molecular mechanisms and physiological consequences of oxidative stress: lessons from a model bacterium. Nat Rev Microbiol 11:443-454.
27. Lorquet F, Goffin P, Muscariello L, Baudry J-B, Ladero V, Sacco M, Kleerebezem M, Hols P. 2004. Characterization and Functional Analysis of the poxB Gene, Which Encodes Pyruvate Oxidase in Lactobacillus plantarum. J Bacteriol 186:3749-3759.
28. Sedewitz B, Schleifer K H, Gotz F. 1984. Purification and biochemical characterization of pyruvate oxidase from Lactobacillus plantarum. J Bacteriol 160:273-278.
29. Solomon E I, Sundaram U M, Machonkin T E. 1996. Multicopper Oxidases and Oxygenases. Chem Rev 96:2563-2606.
30. Claus H, Filip Z. 1997. The evidence of a laccase-like enzyme activity in a Bacillus sphaericus strain. Microbiol Res 152:209-216.
31. Hullo M-F, Moszer I, Danchin A, Martin-Verstraete I. 2001. CotA of Bacillus subtilis Is a Copper-Dependent Laccase. J Bacteriol 183:5426-5430.

32. Schlosser D, Hofer C. 2002. Laccase-catalyzed oxidation of Mn(2+) in the presence of natural Mn(3+) chelators as a novel source of extracellular H(2)O(2) production and its impact on manganese peroxidase. Appl Environ Microbiol 68:3514-3521.
33. Harkin J M, Obst J R. 1973. Syringaldazine, an effective reagent for detecting laccase and peroxidase in fungi. Experientia 29:381-387.
34. Massey V, Muller F, Feldberg R, Schuman M, Sullivan P A, Howell L G, Mayhew S G, Matthews R G, Foust G P. 1969. The Reactivity of Flavoproteins with Sulfite POSSIBLE RELEVANCE TO THE PROBLEM OF OXYGEN REACTIVITY. J Biol Chem 244:3999-4006.
35. Muller F, Massey V. 1969. Flavin-Sulfite Complexes and Their Structures. J Biol Chem 244:4007-4016.
36. Ghisla S, Massey V. 1975. Mechanism of inactivation of the flavoenzyme lactate oxidase by oxalate. J Biol Chem 250:577-584.
37. Slomczynski D, Nakas J P, Tanenbaum S W. 1995. Production and Characterization of Laccase from *Botrytis cinerea* 61-34. Appl Environ Microbiol 61:907-912.
38. Riley M A, Chavan M A. 2007. Bacteriocins—Ecology and Evolution. Springer.
39. Cotter P D, Ross R P, Hill C. 2013. Bacteriocins—a viable alternative to antibiotics? Nat Rev Microbiol 11:95.
40. Marty-Teysset C, Torre F de la, Garel J-R. 2000. Increased Production of Hydrogen Peroxide by *Lactobacillus delbrueckii* subsp. *bulgaricus* upon Aeration: Involvement of an NADH Oxidase in Oxidative Stress. Appl Environ Microbiol 66:262-267.
41. Hertzberger R, Arents J, Dekker H L, Pridmore R D, Gysler C, Kleerebezem M, Mattos M J T de. 2014. $H_2O_2$ Production in Species of the *Lactobacillus acidophilus* Group: a Central Role for a Novel NADH-Dependent Flavin Reductase. Appl Environ Microbiol 80:2229-2239.
42. Tharrington G, Sorrells K M. 1992. Inhibition of *Listeria monocytogenes* by Milk Culture Filtrates from *Lactobacillus delbrueckii* subsp. *lactis*. J Food Prot 55:542-544.
43. Dahiya R S, Speck M L. 1968. Hydrogen Peroxide Formation by Lactobacilli and Its Effect on *Staphylococcus aureusl*. J Dairy Sci 51:1568-1572.
44. Price R J, Lee J S. 1970. Inhibition of *pseudomonas* species by hydrogen peroxide producing lactobacilli. J Milk Food Technol 33:13-18.
45. Goffin P, Muscariello L, Lorquet F, Stukkens A, Prozzi D, Sacco M. Kleerebezem M, Hols P. 2006. Involvement of Pyruvate Oxidase Activity and Acetate Production in the Survival of *Lactobacillus plantarum* during the Stationary Phase of Aerobic Growth. Appl Environ Microbiol 72:7933-7940.
46. Lee S J, Gralla J D. 2001. Sigma38 (rpoS) RNA Polymerase Promoter Engagement via −10 Region Nucleotides. J Biol Chem 276:30064-30071.
47. Pouwels P H, Leer R J. 1993. Genetics of lactobacilli: Plasmids and gene expression. Antonie Van Leeuwenhoek 64:85-107.
48. Compilation and analysis of *Escherichia coli* promoter DNA sequences I Nucleic Acids Research I Oxford Academic.
49. Chang Y-Y, Wang A-Y, Cronan J E. 1994. Expression of *Escherichia coli* pyruvate oxidase (PoxB) depends on the sigma factor encoded by the rpoS(katF) gene. Mol Microbiol 11:1019-1028.
50. Taniai H, Iida K, Seki M, Saito M, Shiota S, Nakayama H, Yoshida S. 2008. Concerted Action of Lactate Oxidase and Pyruvate Oxidase in Aerobic Growth of *Streptococcus pneumoniae*: Role of Lactate as an Energy Source. J Bacteriol 190:3572-3579.
51. Eschenbach D A, Davick P R, Williams B L, Klebanoff S J, Young-Smith K, Critchlow C M, Holmes K K. 1989. Prevalence of hydrogen peroxide-producing *Lactobacillus* species in normal women and women with bacterial vaginosis. J Clin Microbiol 27:251-256.
52. Hawes S E, Hillier S L, Benedetti J, Stevens C E, Koutsky L A, Wolner-Hanssen P, Holmes K K. 1996. Hydrogen Peroxide—Producing Lactobacilli and Acquisition of Vaginal Infections. J Infect Dis 174:1058-1063.
53. Voltan S, Martines D, Elli M, Brun P, Longo S, Porzionato A, Macchi V, D'Inca R, Scarpa M, Palu G, Sturniolo G C, Morelli L, Castagliuolo I. 2008. *Lactobacillus* crispatus M247-Derived $H_2O_2$ Acts as a Signal Transducing Molecule Activating Peroxisome Proliferator Activated Receptor-γ in the Intestinal Mucosa. Gastroenterology 135:1216-1227.
54. Zhu L, Kreth J. 2012. The Role of Hydrogen Peroxide in Environmental Adaptation of Oral Microbial Communities. Oxid Med Cell Longev 2012.
55. Zhu L, Xu Y, Ferretti J J, Kreth J. 2014. Probing Oral Microbial Functionality—Expression of spxB in Plaque Samples. PLOS ONE 9:e86685.
56. Kuramitsu H K, He X, Lux R, Anderson M H. Shi W. 2007. Interspecies Interactions within Oral Microbial Communities. Microbiol Mol Biol Rev MMBR 71:653-670.
57. Kreth J, Zhang Y, Herzberg M C. 2008. Streptococcal Antagonism in Oral Biofilms: *Streptococcus sanguinis* and *Streptococcus gordonii* Interference with *Streptococcus mutans*. J Bacteriol 190:4632-4640.
58. Hillman J D, Socransky S S, Shivers M. 1985. The relationships between streptococcal species and periodontopathic bacteria in human dental plaque. Arch Oral Biol 30:791-795.
59. Kwan R C H, Leung H F, Hon P Y T, Barford J P, Renneberg R. 2005. A screen-printed biosensor using pyruvate oxidase for rapid determination of phosphate in synthetic wastewater. Appl Microbiol Biotechnol 66:377-383.
60. Rahman M A, Park D-S, Chang S-C, McNeil C J, Shim Y-B. 2006. The biosensor based on the pyruvate oxidase modified conducting polymer for phosphate ions determinations. Biosens Bioelectron 21:1116-1124.
61. Situmorang M, Gooding J J, Hibbert D B, Barnett D. The Development of a Pyruvate Biosensor Using Electrodeposited Polytyramine. Electroanalysis 14:17-21.

Example 2: Hydrogen Peroxide-Producing Pyruvate Oxidase from *Lactobacillus delbrueckii* is Catalytically Activated by Phosphotidylethanolamine Pyruvate oxidase (Pox) is an enzyme in the oxidoreductase family. There are hydrogen-peroxide-producing and acetate-producing Pox enzymes. In hydrogen-peroxide-producing Pox enzymes, pyruvate, phosphate, and oxygen are converted to acetylphosphate, carbon dioxide, and hydrogen peroxide with the cofactors flavin adenine dinucleotide (FAD) and thiamine pyrophosphate (TPP) (1). Acetate-producing Pox enzymes catalyze the oxidative decarboxylation of pyruvate to form carbon dioxide and acetate with electrons being transferred directly to the electron transport chain via the membrane-embedded electron carriers (2, 3).

Hydrogen peroxide generating Pox enzymes are produced by multiple different bacteria. Pox enzymes from *Lactobacillus plantarum* and *Streptococcus pneumoniae* are the most well studied. These enzymes form homo-tetrameric structures (4, 5). The role of Pox enzymes in central metabolism is thought to be increasing ATP production in concert with acetate kinase during aerobic metabolism (6). In *S. pneumoniae*, which has no TCA cycle, additional ATP production from glucose is believed to come from this pathway (7). *L. plantarum* Pox is considered to be an important component of the enhanced biomass that is observed in aerobic growth by generating acetyl phosphate as a substrate for acetate kinase (6). In addition, the production of hydrogen peroxide from Pox could also be important on a community level. Since hydrogen peroxide is toxic to some bacteria, Pox activity could confer a fitness advantage to the producer organism. In *S. pneumoniae*, pox-deficient mutants display decreased virulence in a rat model of disease likely through decreased adhesion properties, but also potentially through decreased competition with commensal bacteria (8). *Streptococcus gordonii* and *Streptococcus sanguinis* are known to produce enough hydrogen peroxide primarily through Pox to inhibit the oral pathogen *Streptococcus mutans* (9).

The most well studied acetate-producing Pox is from *Escherichia coli*. *E. coli* Pox is dependent on the same cofactors as other Pox enzymes and is also homo-tetrameric (10). *E. coli* Pox produces acetate and does not utilize oxygen as its final electron acceptor, but rather the membrane embedded ubiquinone 8 electron transport molecule (2). CidC is another acetate-producing Pox enzyme from *Staphylococcus aureus* which transfers electrons to menaquinone and has an important role in cell death pathways (3). PQO from *Corynebacterium glutamicum* also produces acetate and transfers electrons to a quinone (11). One characteristic of *E. coli* Pox, PQO, and CidC is that they are catalytically activated by phospholipids, which is thought to facilitate efficient transfer to membrane electron shuttles by activating the enzyme at a membrane peripheral position (3, 11, 12). Mutants in *E. coli* Pox that disrupt lipid activation of the enzyme are localized to the C-terminal region of the protein. Further biochemical analysis identified a lipid activation helix in the C-terminal region (amino acids 558-568) that upon lipid interaction induce the preceding alpha helix to move out of the active site, which in turn positions phenylalanine 465 into the active site enhancing electron transfer between TPP and FAD (13-15). The phospholipid activation of *E. coli* Pox is a hybrid of K- and V-type allosteric activation where the $k_m$ for pyruvate decreases along with an increase in the enzyme turnover rate Mar. 18, 2020 9:47:00 PM. However, in CidC the activation is V-type where the enzyme turnover rate is substantially increased (3).

In the current study, a hydrogen-peroxide producing Pox enzyme was identified from *L. delbrueckii* that is catalytically activated specifically by phosphotidylethanolamine, a common bacterial membrane component. Further, it was shown that the *L. delbrueckii* Pox adopts a pentameric structure and potentially a dimer of pentamers, which is novel for Pox enzymes. These characteristics are unique for hydrogen-peroxide-producing Pox enzymes and demonstrate substantial variability in the structure and function of Pox from different bacterial species.

Results

Characterization of *L. delbrueckii* Pox

The *E. coli* Pox has been well studied, and it is known that this enzyme is catalytically activated by phospholipids (12, 13, 17). In addition, CidC and POO from *S. aureus* and *C. gluticaticum*, respectively, are other pyruvate oxidases that are lipid activated (3, 11). Another well studied Pox enzyme is from *Lactobacillus plantarum* (1, 6, 18). This enzyme has not been shown to be catalytically activated by phospholipids indicating that there is variability in the catalytic activation of the Pox enzymes.

First, the biochemical properties of the *L. delbrueckii* Pox enzyme were determined. *L. delbrueckii* Pox was previously purified and it was used for subsequent testing (16). The $k_m$ values for pyruvate and phosphate and the $k_{cat}$ value were determined. The $k_m$ for pyruvate and phosphate were 342.2 µM and 8 mM respectively, and the $k_{cat}$ was 0.367 s$^{-1}$ (FIG. 13 and FIG. 22). The optimum pH for several other pyruvate oxidase enzymes is near 5.5 and so the activity of the *L. delbrueckii* Pox at various pHs was tested to determine its pH activity profile. In agreement with other Pox enzymes, the *L. delbrueckii* Pox was most active at the pH range of 5.5 to 6 (FIG. 13C).

*L. delbrueckii* Pox Forms Pentameric Structure in Solution

Figures 14A, 14B:
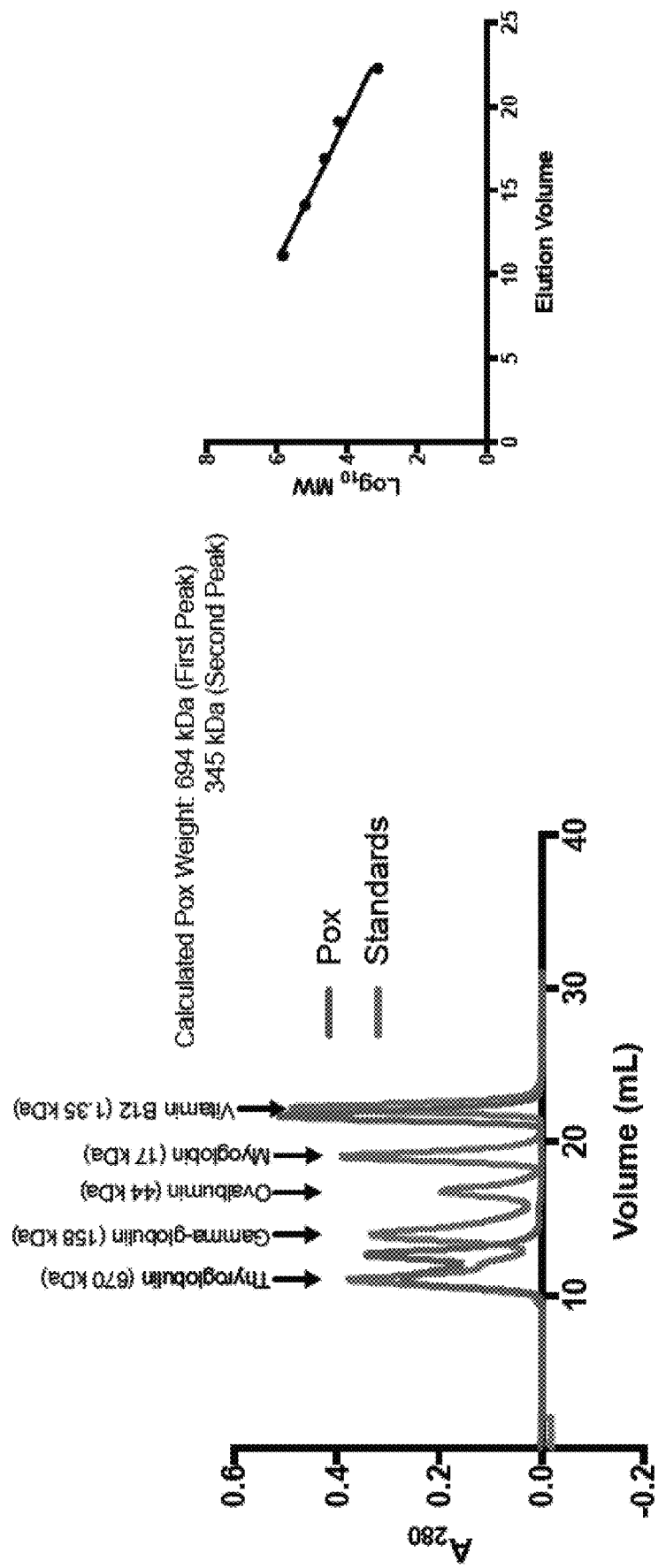
FIGS. 14A-14D demonstrate oligomeric state of *L. delbrueckii* Pox.
Figures 14C, 14D:
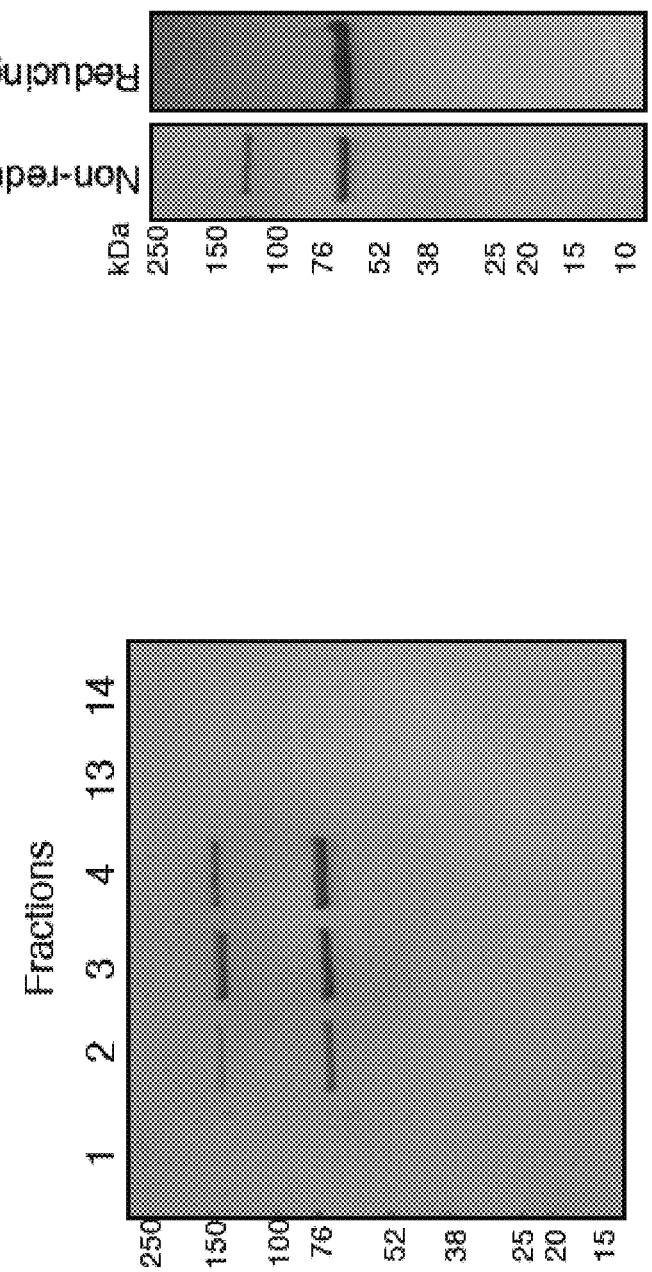

Both the *L. plantarum* and *E. coli* Pox are known to form tetrameric structures (1, 10). To determine whether the *L. delbrueckii* Pox also formed a tetramer, gel filtration chromatography was performed with the purified enzyme. Interestingly, *L. delbrueckii* Pox eluted in two major peaks; the first with a calculated molecular weight of 694 kDa and the second with a calculated molecular weight of 345 kDa (FIGS. 14A-14B). The molecular weight of a *L. delbrueckii* Pox monomer is 68 kDa; therefore, the first peak corresponded to a decamer and the second peak to a pentamer. The last peak corresponded to unbound FAD (FIG. 14A). Analysis of the fractions by non-reducing SDS-PAGE revealed two distinct bands that migrated distances consistent with monomer and dimer forms of the *L. delbrueckii* Pox at approximately 68 kDa and 138 kDa (FIG. 14C). Fractions 13 and 14, which correspond to the last peak from gel filtration, did not contain any protein and also were yellow in color confirming the presence of unbound FAD (FIG. 14C). To confirm that the 138 kDa protein band was in fact a dimer of *L. delbrueckii* Pox, the *L. delbrueckii* Pox was analyzed on non-reducing and a reducing SDS-PAGE. Under reducing conditions, *L. delbrueckii* Pox migrated exclusively as a monomer indicating that the 138 kDa band is a dimer, presumably linked by a disulfide bond at position 72 since it is the only cysteine in the amino acid sequence (FIG. 14D).

Phospholipid Activation of *L. delbrueckii* Pox

Figure 15B:
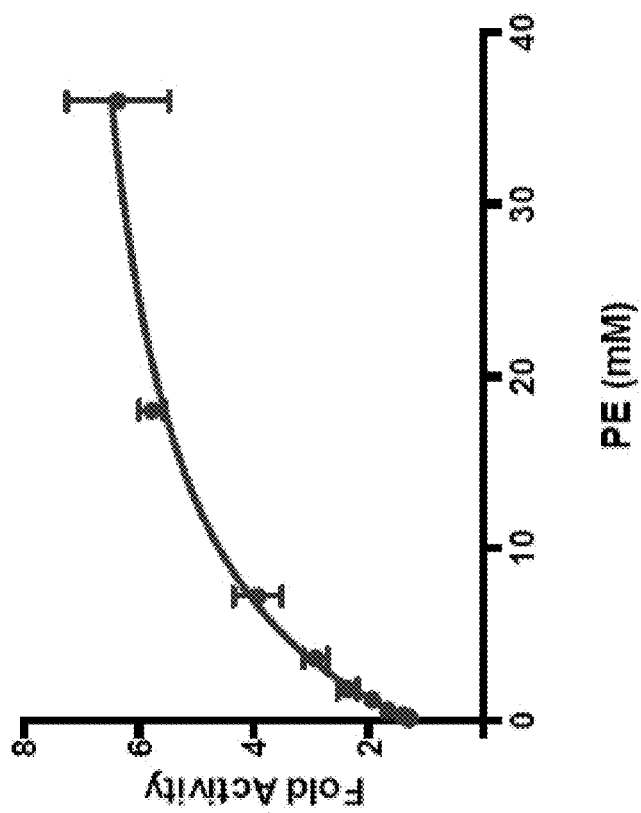
FIGS. 15A-15B demonstrate *L. delbrueckii* Pox is activated specifically by phosphotidylethanolamine.
Figure 15A:
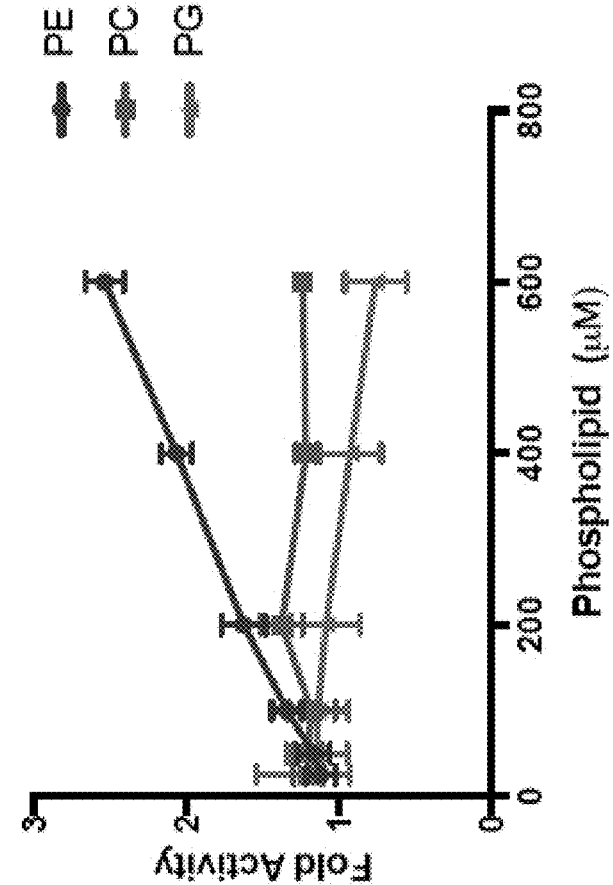

It was hypothesized that *L. delbrueckii* Pox may be activated by phospholipids similar to *E. coli* Pox, CidC, and POO (2, 3, 11). It was tested whether the addition of either phosphotidylethanolamine (PE), phosphotidylcholine (PC), and phosphotidylglycerol (PG) could catalytically activate *L. delbrueckii* Pox. *L. delbrueckii* Pox was catalytically activated specifically by PE, but not PC or PG (FIG. 15A). The phospholipids used contained the same acyl chain structure (16:0-18:1) and only varied in the headgroup indicating that there is specificity in phospholipid activation of *L. delbrueckii*. To determine the full activation profile of *L. delbrueckii* Pox by PE, the fold activity was measured over a wider range of PE concentrations and observed activation upwards of 6-fold relative to the enzyme without PE (FIG. 17B). This level of activation exceeds that of the CidC Pox (3-fold activation) from *S. aureus* (3).

Figures 16A, 16B:
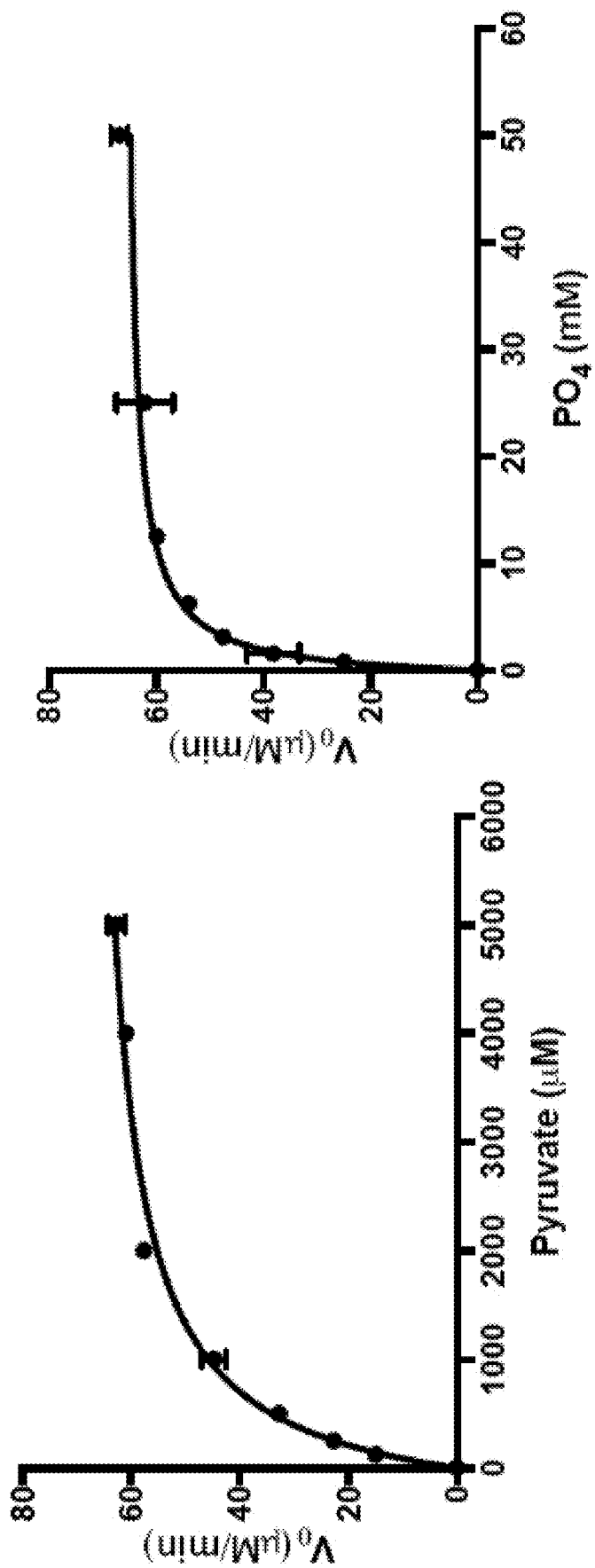
FIGS. 16A-16B demonstrate kinetic parameters of *L. delbrueckii* in the presence of PE.

To gain mechanistic insight into how PE activates the enzyme, the kinetic parameters of *L. delbrueckii* Pox were tested in the presence of PE (FIG. 16). With the addition of PE, the $k_m$ for pyruvate and phosphate were 519.9 µM and 1.25 mM respectively and the $k_{cat}$ was 6.85 s$^{-1}$ (FIG. 23). The approximately 18-fold increase in $k_{cat}$ and decrease in phosphate $k_m$ relative to the enzyme in the absence of PE suggest that these parameters are the primary drivers of catalytic activation, which is consistent with the increase in $k_{cat}$ observed in E. coli Pox and CidC upon phospholipid activation (3, 19). The activation observed here is a hybrid of V- and K-type activation since the $k_{cat}$ increased and the phosphate $k_m$ decreased, which is also consistent with E. coli Pox (15, 19).

Whether L. delbrueckii Pox inserts into PE micelles was also examined. Co-precipitation experiments were performed with L. delbrueckii Pox in the presence and absence of PE. Nearly all of the enzyme remained in the soluble fraction and did not co-precipitate with PE, which is in contrast to E. coli Pox (13) (FIG. 17).

The C-Terminus of L. delbrueckii Pox is Important for Lipid Activation

The C-terminus of E. coli Pox is important for lipid activation of the enzyme (13). To test if the C-terminus was important in the L. delbrueckii Pox, a C-terminal truncation was generated that lacked the last 32 amino acids. The enzyme was purified and tested for its ability to be activated by PE (FIG. 18A). The enzyme had a specific activity of approximately 1.32 U/mg in the absence of PE, which is greater than the specific activity of the full-length enzyme (FIG. 13C and FIG. 18B). This is consistent with the E. coli pox truncation having greater activity partially mimicking lipid activation (20). Furthermore, the Δ32 enzyme was only weakly activated by PE to approximately 2-fold greater than the enzyme without PE compared to an approximately 6-fold activation with the full-length enzyme (FIG. 15B and FIG. 18C). This indicates that the C-terminal sequence is important for the lipid activation of the Pox enzyme.

Discussion

Here, it was demonstrated that the hydrogen-peroxide producing pyruvate oxidase enzyme from L. delbrueckii is catalytically activated specifically by PE, but not other phospholipids, and the last 32 amino acids of the enzyme are important for this activation. It is believed that this is the first hydrogen-peroxide producing Pox enzyme that has been shown to be activated by phospholipids. In addition, it was shown that the L. delbrueckii Pox forms a pentameric structure in solution of which at least two subunits form a disulfide bond between cysteine 72. Other Pox enzymes form tetrameric structures, and there has been no evidence of disulfide bond formation indicating that the L. delbrueckii Pox has a different structure than other Pox enzymes (1, 10).

It is interesting that only PE had an impact on catalytic activity. This suggests that the size, shape, and charge of the phospholipid head group is important for catalytic activation. If the Pox enzyme is interacting with phospholipid that is already incorporated into the membrane, the head group would be exposed to the cytoplasm and be in the closest proximity to the enzyme. The interaction with the cytoplasm-facing ethanolamine likely occurs through the C-terminal 32 amino acids. Similar to the E. coli Pox, it was hypothesized that this interaction induces a conformational shift in the enzyme that enhances electron transfer between FAD and TPP and decreases the phosphate km. This interaction is likely mediated by electrostatic forces. In fact, it is believed that CidC interaction with phospholipids is driven primarily by electrostatic forces suggesting there is interaction with the headgroup (3). Furthermore, PE is known to be an abundant component of bacterial membranes, whereas PC is more commonly a eukaryotic and mammalian membrane component (21, 22). Thus, activation only by PE is reasonable since L. delbrueckii Pox is a bacterial enzyme. Enhanced hydrogen peroxide production by L. delbrueckii could be beneficial in a complex microbial community. In fact, hydrogen peroxide production by Pox has been shown to be important in the inhibition of dental pathogens like P. gingivalis (16).

The pentameric structure of L. delbrueckii Pox is different from what has been observed with E. coli Pox and L. plantarum Pox (1, 10). Based on the gel filtration data, the L. delbrueckii also forms a decamer or a dimer of pentamers, but it is unclear which of these may be occurring. Interestingly, the formation of dimers linked by a disulfide bond was also observed which are a component of the pentameric structure since they were present in fractions with an elution volume consistent with pentameric molecular weight. Therefore, the structure of the pentamer must be comprised of either three monomers and one dimer or one monomer and two dimers.

E. coli Pox lipid activation is a mixture of K- and V-type allosteric activation where the pyruvate $K_m$ decreases and the $k_{cat}$ increases (19, 23). The lipid activation observed with L. delbrueckii Pox was also a mixture of K- and V-type allosteric activation, however, the specific parameters that changed were different. The pyruvate $k_m$ increased slightly while the phosphate $k_m$ decreased. The $K_{cat}$ did increase substantially (18-fold) similar to the E. coli Pox. Since the changes in pyruvate and phosphate $k_m$ could offset one another, it is believed that the lipid activation of L. delbrueckii Pox is primarily driven by increasing the enzyme turnover rate. This is consistent with structural data of E. coli Pox demonstrating that lipid activation's primary effect on the enzyme is to shift a phenylalanine closer to the interface between TPP and FAD to increase the efficiency of electron transfer (15). This is thought to increase the enzyme turnover rate substantially. It is also in agreement with the activation of CidC where the activation of the enzyme was exclusively driven by a 10-fold increase in $k_{cat}$ (3).

E. coli Pox inserts and co-precipitates with lipids in the presence of substrate (13). No co-precipitation of L. delbrueckii Pox with PE were observed under these conditions suggesting that there is no insertion and that the interaction may be transient and/or weak enough such that it cannot withstand centrifugal forces. It may be more necessary for E. coli Pox to insert into the membrane or tightly associate with the membrane since it needs to transfer electrons directly to ubiquinone 8 within the membrane (2). The CidC pyruvate oxidase from S. aureus interacts with phospholipids, but the interaction is believed to be mediated by electrostatic forces indicating that there does not necessarily need to be insertion into the membrane (3). Insertion and tight interaction with the membrane for L. delbrueckii Pox may not be as important since it does not need to transfer electrons to a membrane electron shuttle. The weaker association with the membrane may also be a mechanism to regulate hydrogen peroxide production. If the association were too strong or there was insertion into the membrane, excessive hydrogen peroxide production may intoxicate the cell. Alternatively, a single interaction with the phospholipid could shift the L. delbrueckii Pox into the activated conformation, which would not necessitate continuous interaction or insertion for lipid activation. In fact, studies of the E. coli Pox suggest that lipid activators may lock the enzyme into the activated conformation (23).

E. coli Pox, CidC, and PQO are the only known lipid-activated Pox enzymes (3, 11, 13). These Pox enzymes likely evolved this ability so that it is most active near or at the membrane where it can readily transfer electrons to a membrane electron shuttle (3, 15). It was demonstrated here and previously that *L. delbrueckii* Pox generates hydrogen peroxide and as such it transfers electrons to oxygen (16). The lipid activation characteristic of *E. coli* Pox is logical based upon its final electron acceptor. However, the utility of lipid activation of *L. delbrueckii* Pox is less clear considering that it does not transfer electrons to an intramembrane ubiquinone or electron shuttle. One hypothesis for this observation is that the lipid activation of *L. delbrueckii* Pox may be a vestigial element from an ancestral Pox that utilized ubiquinone 8 as an electron acceptor and was more similar to the *E. coli* Pox. If the ancestral Pox enzyme arose during a period in evolutionary history where there was oxygen present, then the ancestral enzyme may have been lipid activated to ensure electron transfer to a membrane ubiquinone rather than inadvertent transfer to oxygen. This characteristic could have been preserved in later hydrogen peroxide-producing Pox enzymes because it would not have necessarily been disadvantageous for the bacterium. Thus, there would have been little to no selective pressure to lose lipid activation of the enzyme. In fact, it could be advantageous for a hydrogen peroxide producing pox to retain lipid activation.

Hydrogen peroxide production can be self-inhibitory and potentially damage the producing cell. The lipid activation of a hydrogen peroxide-producing Pox could be beneficial because it would position hydrogen peroxide production at a peripheral point of the cell. Diffusion of hydrogen peroxide from this point would subject the interior of the cell to less hydrogen peroxide and excrete more than if the enzyme were positioned in the middle of the cell. Persevering the lipid-activation of the Pox enzyme in this case may reduce the self-toxicity of hydrogen peroxide production.

Described herein is the first hydrogen-peroxide producing Pox enzyme that is activated by the phospholipid phosphotidylethanolamine. Also demonstrated is a different oligomeric structure than other known Pox enzymes. Together, these data demonstrate that Pox enzymes from different bacterial species can vary in their structure and function.

Material and Methods
Pyruvate Oxidase

Pyruvate oxidase enzyme or pyruvate:oxygen 2-oxidoreductase (phosphorylating) (EC 1.2.3.3) was derived from *Lactobacillus delbrueckii* STYM1 strain (16).

Purification of *L. delbrueckii* Pox Δ32

The *L. delbrueckii* deletion mutant was PCR amplified from STYM1 genomic DNA using the primers listed in FIG. 24. The PCR product was ligated into the pFLAG-CTC vector (Sigma, St. Louis, Mo.) using the NdeI and XhoI restriction sites. The Product was transformed into DH5α *E. coli* and the construct was confirmed by PCR and sequencing. The construct was transformed into LOBSTR *E. coli*, in which the *L. delbrueckii* Δ32 Pox was expressed as a C-terminal $His_6$-Pox. A starter culture was diluted 1:100 into 40 mL of LB supplemented with 100 µg/mL of carbenicillin and grown at 37° C. until the $OD_{600}$ reached 0.4-0.8. The cells were cooled on ice for 10 minutes and 1 mM isopropyl-β-D-thiogalactopyranoside (IPTG) (Sigma, St. Louis, Mo.) was added and the cells incubated at 25° C. with shaking for 20 hours. The cells were harvested by centrifugation at 3200×g for 20 minutes at 4° C. and resuspended in 1 mL 20 mM Bis-Tris 150 mM NaCl pH 7 with EDTA-free cOmplete protease inhibitor cocktail. The cells were lysed by sonication on ice and the soluble cell lysate was harvested by centrifugation at 16000×g for 15 minutes at 4° C. The soluble cell lysate was filtered through a 0.22 µm PVDF filter and applied to a 1 mL bed volume of HisPure Ni-NTA resin (Thermofisher, Waltham, Mass.). The column was washed twice with two column volumes of buffer containing 25 mM imidazole (Fisher, Pittsburgh, Pa.) and the bound protein was eluted from the column in buffer containing 250 mM imidazole. Protein purity was assessed by SDS-PAGE and Coomassie staining.

Pyruvate Oxidase Activity Assay and Kinetic Parameters

Pyruvate oxidase activity was measured as previously described (16). Briefly, 50 mM sodium pyruvate, 15 µM FAD, 300 µM TPP, 0.03% N-ethyl-N-(2-hydroxy-3-sulfopropyl)-m-toluidine (sigma), 0.015% 4-aminoantipyrine (sigma), and 33 µg/mL horseradish peroxidase (Sigma) were combined with purified pox enzyme. After a 10-minute incubation at room temperature, sodium phosphate pH 5.6 was added to 50 mM final concentration to initiate the reaction. The formation of a quinoneimine dye at 25° C. was measured by an increase in absorbance at 550 nm and the specific activity was calculated as described. 1 unit of Pox activity is defined as the production of 1 µmol of hydrogen peroxide per minute and this was converted to µM/min for kinetic analysis.

For $k_m$ determination of pyruvate and phosphate and determination of $k_{cat}$, dilutions of substrate were used instead of the 50 mM concentration. Enzyme concentration was 1.76 µM. Vo for each substrate concentration was plotted and the data were fitted using Prism software $k_{cat}$ non-linear regression function. For $k_m$ and $k_{cat}$ determination in the presence of phosphotidylethanolamine (PE), PE was used at a concentration of 7.2 mM and the enzyme concentration was 170 nM.

Phospholipid Activation Assay

Phosphotidylethanolamine (16:0-18:1) (Avanti Lipids), Phosphotidylcholine (16:0-18:1) (Avanti Lipids), and Phosphotidylglycerol (16:0-18:1) (Avanti Lipids) dissolved in chloroform were evaporated under a steady stream of argon gas and dried in a vacuum desiccator for 1 hour to evaporate residual chloroform. The phospholipids were resuspended in 20 mM Bis-Tris 150 mM NaCl pH 6 and incubated at 37° C. with shaking at 225 rpm for 30 minutes. The suspension was vortexed for 30 seconds and vortexed immediately prior to each use.

Phospholipids were added to the pyruvate oxidase assay mixture at various concentrations and enzyme activity was measured as described above. Fold activity was calculated relative to enzyme activity without phospholipid.

Gel Filtration Analysis

Prior to analysis of the *L. delbrueckii* Pox, protein standards were mixed together and applied to the Superdex 200 column (GE healthcare). The protein standards were thyroglobulin (670 kDa), gamma-globulin (150 kDa), ovalbumin (44 kDa), myoglobulin (17 kDa), and vitamin B12 (1.35 kDa). A standard curve was plotted using the peak elution volume for each standard versus the $Log_{10}$ of the molecular weight in daltons. 840 µg of purified *L. delbrueckii* Pox was incubated in the presence of 50 mM pyruvate, 300 µM TPP, and 15 µM FAD for 10 minutes at room temperature prior to application to the column. The absorbance at 280 nm was recorded over the elution. 1 mL fractions were collected after the void volume of 10 mL until the end of the elution. The peak volume for the Pox fractions was used to calculate the molecular weight according to the standard curve.

*L. delbrueckii* Pox in each fraction from gel filtration was visualized after non-reducing SDS-PAGE analysis with Coomassie staining. For reducing SDS-PAGE analysis, 5% β-mercaptoethanol was included in the sample buffer.

PE Co-Sedimentation

PE was prepared as described above for activation experiments. 3 μg of *L. delbrueckii* Pox was incubated with 50 mM pyruvate, 300 μM TPP, and 15 μM FAD with either 1 mM PE or no PE for 30 minutes at room temperature. The PE fraction was precipitated by centrifugation at 16,000×g for 20 minutes at 4° C. The supernatant was aspirated as the soluble fraction and the PE pellet was resuspended in an equal amount of buffer. The fractions were visualized by Coomassie staining after SDS-PAGE.

REFERENCES

1. Sedewitz B, Schleifer K H, Götz F. 1984. Purification and biochemical characterization of pyruvate oxidase from *Lactobacillus plantarum*. J Bacteriol 160:273-278.
2. Cunningham C C, Hager L P. 1975. Reactivation of the lipid-depleted pyruvate oxidase system from *Escherichia coli* with cell envelope neutral lipids. J Biol Chem 250: 7139-7146.
3. Zhang X, Bayles K W, Luca S. 2017. *Staphylococcus aureus* CidC Is a Pyruvate:Menaquinone Oxidoreductase. Biochemistry 56:4819-4829.
4. Muller Y A, Schulz G E. 1993. Structure of the thiamine- and flavin-dependent enzyme pyruvate oxidase. Science 259:965-967.
5. Ramos-Montañez S, Tsui H-C T, Wayne K J, Morris J L, Peters L E, Zhang F, Kazmierczak K M, Sham L-T, Winkler M E. 2008. Polymorphism and regulation of the spxB (pyruvate oxidase) virulence factor gene by a CBS-HotDog domain protein (SpxR) in serotype 2 *Streptococcus pneumoniae*. Mol Microbiol 67:729-746.
6. Lorquet F, Goffin P, Muscariello L, Baudry J-B, Ladero V, Sacco M, Kleerebezem M, Hols P. 2004. Characterization and Functional Analysis of the poxB Gene, Which Encodes Pyruvate Oxidase in *Lactobacillus plantarum*. J Bacteriol 186:3749-3759.
7. Taniai H, Iida K, Seki M, Saito M, Shiota S, Nakayama H, Yoshida S. 2008. Concerted Action of Lactate Oxidase and Pyruvate Oxidase in Aerobic Growth of *Streptococcus pneumoniae*: Role of Lactate as an Energy Source. J Bacteriol 190:3572-3579.
8. Spellerberg B, Cundell D R, Sandros J, Pearce B J, Idänpään-Heikkilä I, Rosenow C, Masure H R. 1996. Pyruvate oxidase, as a determinant of virulence in *Streptococcus pneumoniae*. Mol Microbiol 19:803-813.
9. Kreth J, Zhang Y, Herzberg M C. 2008. Streptococcal Antagonism in Oral Biofilms: *Streptococcus sanguinis* and *Streptococcus gordonii* Interference with *Streptococcus mutans*. J Bacteriol 190:4632-4640.
10. Wang A Y, Chang Y Y, Cronan J E. 1991. Role of the tetrameric structure of *Escherichia coli* pyruvate oxidase in enzyme activation and lipid binding. J Biol Chem 266:10959-10966.
11. Schreiner M E, Eikmanns B J. 2005. Pyruvate:Quinone Oxidoreductase from *Corynebacterium glutamicum*: Purification and Biochemical Characterization. J Bacteriol 187:862-871.
12. Chang Y-Y, Cronan J E. 1984. An *Escherichia coli* mutant deficient in pyruvate oxidase activity due to altered phospholipid activation of the enzyme. Proc Natl Acad Sci 81:4348-4352.
13. Grabau C, Chang Y Y, Cronan J E. 1989. Lipid binding by *Escherichia coli* pyruvate oxidase is disrupted by small alterations of the carboxyl-terminal region. J Biol Chem 264:12510-12519.
14. Cunningham C C, Hager L P. 1971. Crystalline Pyruvate Oxidase from *Escherichia coli* III. PHOSPHOLIPID AS AN ALLOSTERIC EFFECTOR FOR THE ENZYME. J Biol Chem 246:1583-1589.
15. Neumann P, Weidner A, Pech A, Stubbs M T, Tittmann K. 2008. Structural basis for membrane binding and catalytic activation of the peripheral membrane enzyme pyruvate oxidase from *Escherichia coli*. Proc Natl Acad Sci 105:17390-17395.
16. Cornacchione L P, Klein B A, Duncan M J, Hu L T. 2019. Interspecies inhibition of *Porphyromonas gingivalis* by yogurt-derived *Lactobacillus delbrueckii* require active pyruvate oxidase. Appl Environ Microbiol AEM.01271-19.
17. Grabau C, Cronan J E. 1986. In vivo function of *Escherichia coli* pyruvate oxidase specifically requires a functional lipid binding site. Biochemistry 25:3748-3751.
18. Risse B, Stempfer G, Rudolph R, Möllering H, Jaenicke R. 1992. Stability and reconstitution of pyruvate oxidase from *Lactobacillus plantarum*: Dissection of the stabilizing effects of coenzyme binding and subunit interaction. Protein Sci 1:1699-1709.
19. Bertagnolli B L, Hager L P. 1991. Activation of *Escherichia coli* pyruvate oxidase enhances the oxidation of hydroxyethylthiamin pyrophosphate. J Biol Chem 266: 10168-10173.
20. Recny M A, Grabau C, Cronan J E, Hager L P. 1985. Characterization of the alpha-peptide released upon protease activation of pyruvate oxidase. J Biol Chem 260: 14287-14291.
21. Vance J E. 2015. Phospholipid Synthesis and Transport in Mammalian Cells. Traffic 16:1-18.
22. Zhang Y-M, Rock C O. 2008. Membrane lipid homeostasis in bacteria. Nat Rev Microbiol 6:222-233.
23. Mather M W, Gennis R B. 1985. Kinetic studies of the lipid-activated pyruvate oxidase flavoprotein of *Escherichia coli*. J Biol Chem 260:16148-16155.

What is claimed is:

1. A method of treating periodontal disease in a subject comprising administering a bacterial strain engineered to overexpress a LDBND_1487 pyruvate oxidase (pox) enzyme to the subject.

2. The method of claim 1, wherein the bacterial strain is *Lactobacillus delbrueckii*.

3. The method of claim 1, wherein the bacterial strain is a *Streptococcus* bacterial strain or a *Corynebacterium* bacterial strain.

4. The method of claim 1, wherein the bacterial strain is a *Streptococcus* bacterial strain.

5. The method of claim 4, wherein the *Streptococcus* bacterial strain is selected from the group consisting of *Streptococcus sanguinis, Streptococcus gordonii, Streptococcus oralis, Streptococcus mitis, Streptococcus infantis, Streptococcus parasanguinis, Streptococcus australis, Streptococcus cristatus, Streptococcus intermedius, Streptococcus salivarius, Streptococcus peroris, Streptococcus constellatus, Streptococcus ratti*, and *Streptococcus sobrinus*.

6. The method of claim 1, wherein the bacterial strain is a *Corynebacterium* bacterial strain.

7. The method of claim 6, wherein the *Corynebacterium* bacterial strain is selected from the group consisting of *Corynebacterium matruchotii* and *Corynebacterium durum*.

8. The method of claim 1, wherein the bacterial strain inhibits growth of *Porphyromonas gingivalis*.

9. The method of claim 1, wherein the bacterial strain produces amounts of hydrogen peroxide inhibitor to *Porphyromonas gingivalis*, thereby treating the periodontal disease in the subject.

10. The method of claim 1, wherein administration of the bacterial strain to the subject corrects dysbiosis of the oral microbiota.

11. The method of claim 1, wherein the LDBND_1487 pox enzyme is activated by a phospholipid.

12. The method of claim 1, wherein the LDBND_1487 pox enzyme is activated by phosphotidylethanolamine.

* * * * *

SEQUENCE LISTING

<160> NUMBER OF SEQ ID NOS: 22

<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
cccattggga ataataacct ttatacctg                                    29

-continued

<210> SEQ ID NO 2
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 2
ggccacgcgt gcactagtac ntacng                                        26

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ggtctctgca attgctcgag                                               20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ggccacgcgt gcactagtac                                               20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
caagcagaag acggcatacg                                               20

<210> SEQ ID NO 6
<211> LENGTH: 34
<212> TYPE: DNA
<213> ORGANISM: Artificial
<220> FEATURE:
<223> OTHER INFORMATION: primer

<400> SEQUENCE: 6
gaccatgcta gctctttttgc cgcagagctg attc                              34

<210> SEQ ID NO 7
<211> LENGTH: 40
<212> TYPE: DNA
<213> ORGANISM: Artificial
<220> FEATURE:
<223> OTHER INFORMATION: primer

<400> SEQUENCE: 7
gaccatgcat gctcagaaga aaagtattcc tatccggtag                         40

```
<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
ctggatgacc cagaattcgt gaag                                          24

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
gaagttgctt gaacttgcaa tgcttc                                        26

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
gtttcccagg tggttctttt gac                                           23

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ccatgcagac accaagcttg                                               20

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12
agatatcata tggcaaaaat taagggcgca aac                                33

<210> SEQ ID NO 13
<211> LENGTH: 63
<212> TYPE: DNA
<213> ORGANISM: Artificial
<220> FEATURE:
<223> OTHER INFORMATION: primer

<400> SEQUENCE: 13
aattccctcg agttagtgat ggtgatggtg atgacttccg tgagaagcac ctgaagtagt    60
gtc                                                                 63

<210> SEQ ID NO 14
<211> LENGTH: 36
<212> TYPE: DNA
```

```
<213> ORGANISM: Artificial
<220> FEATURE:
<223> OTHER INFORMATION: primer

<400> SEQUENCE: 14
agatatcata tggcaaaaat taagggcgca aacgct                           36

<210> SEQ ID NO 15
<211> LENGTH: 56
<212> TYPE: DNA
<213> ORGANISM: Artificial
<220> FEATURE:
<223> OTHER INFORMATION: primer

<400> SEQUENCE: 15
aattccctcg agttagtgat ggtgatggtg atgacttccg tgagaagcac ctgaac     56

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
agatatcata tggcaaaaat taagggcgca aac                              33

<210> SEQ ID NO 17
<211> LENGTH: 63
<212> TYPE: DNA
<213> ORGANISM: Artificial
<220> FEATURE:
<223> OTHER INFORMATION: primer

<400> SEQUENCE: 17
aattccctcg agttagtgat ggtgatggtg atgacttcct gcacctgaag ccgcgtcaat 60
ttc                                                              63

<210> SEQ ID NO 18
<211> LENGTH: 171
<212> TYPE: PRT
<213> ORGANISM: Artificial
<220> FEATURE:
<223> OTHER INFORMATION: LDBND_1487 Pox

<400> SEQUENCE: 18
```

Met Ser Gln Glu Leu Leu Thr Leu Ala Arg Tyr Asn Met His Val Leu
1               5                   10                  15

Thr Val Val Phe Thr Asn Glu Thr Leu Gly Phe Ile Glu Ala Glu Gln
            20                  25                  30

Arg Asp Glu Ser Asn Gln Pro Leu Ser Gly Val Ile Ile Pro Asp Asn
        35                  40                  45

Asp Trp Ala Lys Val Ala Glu Gly Met Asn Met Lys Ala Phe Thr Val
    50                  55                  60

His Asp Lys Ala Glu Phe Gln Ala Ala Val Glu Glu Trp Lys Lys Met
65                  70                  75                  80

Asp Gly Pro Ala Phe Ile Asp Val Lys Tyr Thr Lys His Met Ala Tyr
                85                  90                  95

Ser Thr Glu Leu Asn Thr Leu Asp Asp Pro Glu Phe Val Lys Tyr Tyr
            100                 105                 110

His Ala Glu Ala Leu His Pro Phe Ser Tyr Phe Ala Glu Lys Phe Gly
        115                 120                 125

```
Leu Glu Ile Asp Ala Ala Ser Gly Ala Ser Gly His Ser Glu Asp Lys
            130                 135                 140

Ala Glu Ala Leu Gln Val Gln Ala Thr Ser Ser Ala Ser Thr Pro Glu
145                 150                 155                 160

Thr Ala Pro Asp Thr Thr Ser Gly Ala Ser His
                165                 170

<210> SEQ ID NO 19
<211> LENGTH: 165
<212> TYPE: PRT
<213> ORGANISM: Artificial
<220> FEATURE:
<223> OTHER INFORMATION: LDBND_2051 Pox

<400> SEQUENCE: 19

Met Ser Gln Glu Leu Leu Thr Leu Ala Arg Tyr Asn Met His Val Leu
1               5                   10                  15

Thr Val Val Phe Thr Asn Glu Thr Leu Gly Phe Ile Glu Ala Glu Gln
            20                  25                  30

Arg Asp Glu Ser Asn Gln Pro Leu Ser Gly Val Ile Leu Pro Asp Asn
        35                  40                  45

Asp Trp Ala Lys Val Ala Glu Gly Met Asn Met Lys Ala Phe Thr Val
50                  55                  60

His Asp Lys Ala Glu Phe Gln Ala Ala Val Glu Glu Trp Lys Lys Met
65                  70                  75                  80

Asp Gly Pro Ala Phe Ile Asp Val Lys Tyr Thr Lys His Met Ala Tyr
                85                  90                  95

Ser Thr Glu Leu Asn Thr Leu Asp Asp Pro Glu Phe Val Lys Tyr Tyr
            100                 105                 110

His Ala Glu Ala Leu His Pro Phe Ser Tyr Phe Ala Gly Lys Phe Gly
        115                 120                 125

Leu Glu Ile Asp Ala Ala Ser Gly Ala Ser Gly His Ser Glu Asp Lys
    130                 135                 140

Ala Asp Ala Leu Ser Ala Ser Ser Pro Glu Thr Ala Pro Asp Thr Ser
145                 150                 155                 160

Ser Gly Ala Ser His
                165

<210> SEQ ID NO 20
<211> LENGTH: 106
<212> TYPE: PRT
<213> ORGANISM: Artificial
<220> FEATURE:
<223> OTHER INFORMATION: Consensus sequence

<400> SEQUENCE: 20

Cys Gly Ala Met Thr Ala Trp Met Met Thr Thr Arg Ala Thr Met Thr
1               5                   10                  15

Trp Lys Tyr Ser Arg Cys Asn Asn Thr Lys Thr Thr Gly Ala Tyr Ala
            20                  25                  30

Gly Cys Arg Cys Thr Thr Arg Cys Ala Arg Arg Asn Ala Gly Thr Ser
        35                  40                  45

Trp Ala Trp Ala Ala Trp Thr Arg Thr Asn Arg Ser Thr Lys Thr Ala
50                  55                  60

Ala Lys Trp Ala Ala Asn Asn Asn Cys Thr Lys Thr Asn Asn Ala Ala
65                  70                  75                  80

Gly Lys Ala Ala Thr Trp Ala Trp Thr Thr Lys Thr Ala Ala Gly Gly
```

```
                     85                  90                  95
Ala Gly Ala Thr Thr Cys Ala Cys Thr Thr
                100                 105

<210> SEQ ID NO 21
<211> LENGTH: 100
<212> TYPE: DNA
<213> ORGANISM: Artificial
<220> FEATURE:
<223> OTHER INFORMATION: LDBND_1487 pox

<400> SEQUENCE: 21
ataaaattaa tcttttcaca atgttgacag cgcttacagg gagtctataa ttattactgt      60
aagtaacttt taaaggaatt aattgtaagg agattcactt                          100

<210> SEQ ID NO 22
<211> LENGTH: 100
<212> TYPE: DNA
<213> ORGANISM: Artificial
<220> FEATURE:
<223> OTHER INFORMATION: LDBND_2051 pox

<400> SEQUENCE: 22
cgactatcct tgatatagcg gcttttgata gcacttgcaa aagtgaaaaa atgtggttta      60
ataaagggct gtaagtaata atttttaagg agattcactt                          100
```